(12) United States Patent
Bouyssou et al.

(10) Patent No.: US 7,429,583 B2
(45) Date of Patent: Sep. 30, 2008

(54) BETAMIMETICS FOR THE TREATMENT OF RESPIRATORY COMPLAINTS

(75) Inventors: Thierry Bouyssou, Mietingen (DE); Enzo Cereda, Novi Ligure (IT); Christoph Hoenke, Ingelheim (DE); Ingo Konetzki, Warthausen (DE); Philipp Lustenberger, Warthausen (DE); Andreas Schnapp, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 110 days.

(21) Appl. No.: 11/222,149

(22) Filed: Sep. 8, 2005

(65) Prior Publication Data

US 2006/0063817 A1    Mar. 23, 2006

(30) Foreign Application Priority Data

Sep. 21, 2004    (DE)    .................. 10 2004 045 648

(51) Int. Cl.
*C07D 417/02*    (2006.01)
*A61K 31/428*    (2006.01)

(52) U.S. Cl. .............. 514/230.5; 544/105; 546/158; 548/221; 514/312; 514/376

(58) Field of Classification Search .............. 544/105; 514/230.5, 312, 376; 546/158; 548/221
See application file for complete search history.

(56) References Cited

U.S. PATENT DOCUMENTS 4,154,829 A  *  5/1979  Mentrup et al. .......... 514/229.8
4,378,361 A      3/1983  Schromm et al.
4,581,367 A      4/1986  Schromm et al.
4,647,563 A      3/1987  Schromm et al.
7,160,882 B2     1/2007  Bouyssou et al.
2007/0066609 A1  3/2007  Bouyssou et al.

FOREIGN PATENT DOCUMENTS

| CA | 2552784 | 8/2005 |
|---|---|---|
| DE | 2833140 | 2/1980 |
| DE | 102004003428 | 8/2005 |
| WO | WO 2005070908 | 8/2005 |

* cited by examiner

*Primary Examiner*—Kahsay T Habte
(74) *Attorney, Agent, or Firm*—Michael P. Morris; Mary-Ellen M. Devlin; Edouard G. Lebel

(57) ABSTRACT

The present invention relates to compounds of formula 1 wherein the groups n, m, B, X and $R^1$ may have the meanings given in the claims and specification, processes for preparing them and their use as pharmaceutical compositions, particularly as pharmaceutical compositions for the treatment of respiratory complaints.

25 Claims, No Drawings

BETAMIMETICS FOR THE TREATMENT OF RESPIRATORY COMPLAINTS

This application claims priority benefit from DE 10 2004 045 648.8, filed Sep. 21, 2004.

Betamimetics (β-adrenergic substances) are known from the prior art. For example, reference is made in this respect to the disclosure of U.S. Pat. Nos. 4,460,581 and 4,154,829, proposing betamimetics for the treatment of a wide variety of ailments.

For drug treatment of diseases it is often desirable to prepare medicaments with a longer duration of activity. As a rule, this ensures that the concentration of the active substance in the body needed to achieve the therapeutic effect is guaranteed for a longer period without the need to re-administer the drug at frequent intervals. Moreover, giving an active substance at longer time intervals contributes to the wellbeing of the patient to a high degree.

It is particularly desirable to prepare a pharmaceutical composition which can be used therapeutically by administration once a day (single dose). The use of a drug once a day has the advantage that the patient can become accustomed relatively quickly to regularly taking the drug at certain times of the day.

The aim of the present invention is therefore to prepare betamimetics which on the one hand provide a therapeutic benefit in the treatment of respiratory complaints and are also characterised by a longer duration of activity and can thus be used to prepare pharmaceutical compositions with a longer duration of activity. A particular aim of the invention is to prepare betamimetics which, by virtue of their long-lasting effect, can be used to prepare a drug for administration once a day. In addition to these aims, a further objective of the invention is to provide such betamimetics which are not only exceptionally potent but are also characterised by a high degree of selectivity with respect to the $\beta_2$-adreno-receptor.

DESCRIPTION OF THE INVENTION

Surprisingly it has been found that the abovementioned problems are solved by compounds of formula 1. Accordingly, the present invention relates to compounds of formula 1

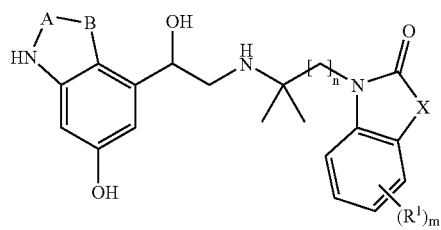

wherein n denotes 1, 2, 3 or 4;
m denotes 1, 2, 3 or 4;
X denotes $CH_2$, CO, $NR^2$, S or O;
A denotes a double-bonded group selected from among CO, SO, $SO_2$;
B denotes a double-bonded group selected from among O, S, $CH_2$, $CR^3R^4$—O, $CR^3R^4$—S, $NR^5$, $CR^3R^4$—$NR^5$, CH=CH or $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH or COO—$C_{1-4}$-alkyl;
$R^2$ denotes H, $C_{1-6}$-alkyl, $C_{1-4}$-alkylene-$C_6$-$C_{10}$-aryl or $C_{1-4}$-alkylene-$C_{3-6}$-cycloalkyl, preferably H or $C_{1-6}$-alkyl;
$R^3$ denotes H or $C_{1-6}$-alkyl;
$R^4$ denotes H or $C_{1-6}$-alkyl;
$R^5$ denotes H or $C_{1-6}$-alkyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

In the case of repeatedly occurring groups $R^1$ (=m>1) these may have the same or different meanings selected from the definitions given for $R^1$.

Preferred compounds of formula 1 above are those wherein
A denotes CO;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 1, 2 or 3; preferably 2 or 3
m denotes 1, 2, 3 or 4; preferably 1, 2 or 3;
X denotes $CH_2$, CO, $NR^2$, S or O;
A denotes CO;
B denotes a double-bonded group selected from among O, S, $CH_2$, $CR^3R^4$—O, $CR^3R^4$—S, $NR^5$, $CR^3R^4$—$NR^5$, CH=CH or $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH, COO—$C_{1-4}$-alkyl; preferably H, $C_{1-6}$-alkyl, $C_{1-6}$-haloalkyl, $C_{3-6}$-cycloalkyl, halogen, OH, CN, $NO_2$, O—$C_{1-6}$-alkyl, COOH or COO—$C_{1-4}$-alkyl;
$R^2$ denotes H, $C_{1-4}$-alkyl, $C_{1-2}$-alkylene-$C_{3-6}$-cycloalkyl, phenylethyl or benzyl, preferably H, $C_{1-4}$-alkyl, $C_{3-6}$-cycloalkyl-methyl, particularly preferably H, methyl or cyclopropylmethyl;
$R^3$ denotes H or $C_{1-4}$-alkyl; preferably H or methyl;
$R^4$ denotes H or $C_{1-4}$-alkyl; preferably H or methyl;
$R^5$ denotes H or $C_{1-4}$-alkyl; preferably H or methyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 1, 2 or 3; preferably 2 or 3
m denotes 1, 2, 3 or 4; preferably 1, 2 or 3;
X denotes $CH_2$, CO, $NR^2$, S or O;
A denotes CO;
B denotes a double-bonded group selected from among O, S, $CH_2$, $CR^3R^4$—O, $CR^3R^4$—S, $NR^5$, $CR^3R^4$—$NR^5$, CH=CH or $CH_2$—$CH_2$;
$R^1$ denotes H, $C_{1-4}$-alkyl, $C_{1-4}$-haloalkyl, cyclopropyl, cyclohexyl, halogen, OH, O—$C_{1-4}$-alkyl, COOH or COOMe;
$R^2$ denotes H, $C_{1-4}$-alkyl, $C_{3-6}$-cycloalkyl-methyl, particularly preferably H, methyl or cyclopropylmethyl;
$R^3$ denotes H or $C_{1-4}$-alkyl, preferably H or methyl;
$R^4$ denotes H or $C_{1-4}$-alkyl, preferably H or methyl;
$R^5$ denotes H or $C_{1-4}$-alkyl, preferably H or methyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 2 or 3;
m denotes 1, 2 or 3;
X denotes $CH_2$, CO, $NR^2$, S or O;
A denotes CO;
B denotes a double-bonded group selected from among O, S, $CH_2$, $CR^3R^4$—O, $CR^3R^4$—S, $NR^5$, $CR^3R^4$—$NR^5$, CH=CH or $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H, methyl, ethyl, propyl, cyclopropylmethyl, preferably H or methyl;
$R^3$ denotes H, methyl, ethyl or propyl, preferably H;
$R^4$ denotes H, methyl, ethyl or propyl, preferably H;
$R^5$ denotes H, methyl, ethyl or propyl, preferably H;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 2 or 3;
m denotes 1, 2 or 3;
X denotes $CH_2$, CO, $NR^2$, S or O;
A denotes CO;
B denotes a double-bonded group selected from among O, S, $CH_2$, $CR^3R^4$—O, $CR^3R^4$—S, $NR^5$, $CR^3R^4$—$NR^5$, CH=CH or $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H, methyl, ethyl or propyl;
$R^3$ denotes H or methyl, preferably H;
$R^4$ denotes H or methyl, preferably H;
$R^5$ denotes H or methyl, preferably H;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 2 or 3;
m denotes 1, 2 or 3;
X denotes $CH_2$, CO, $NR^2$, S or O;
A denotes CO;
B denotes a double-bonded group selected from among $CH_2$—O, CH=CH or $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H, methyl, ethyl or propyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 2 or 3;
m denotes 1 or 2;
X denotes $CH_2$, CO, $NR^2$, S or O;
A denotes CO;
B denotes a double-bonded group selected from among $CH_2$—O, CH=CH or $CH_2$—$CH_2$;
$R^1$ denotes H, methyl, ethyl, propyl, $CF_3$, $CH_2F$ or $CH_2CF_3$;
$R^2$ denotes H, methyl, ethyl or propyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 2 or 3;
m denotes 1;
X denotes $CH_2$, CO, $NR^2$, S or O;
A denotes CO;
B denotes a double-bonded group selected from among $CH_2$—O, CH=CH or $CH_2$—$CH_2$;
$R^1$ denotes H, methyl or $CF_3$;
$R^2$ denotes H or methyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
X denotes $NR^2$ or O; wherein $R^2$ has the meaning given above, preferably H or $C_{1-4}$-alkyl; particularly preferably H, methyl, ethyl or propyl, particularly preferably H or methyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Preferred compounds of formula 1 above are those wherein
n denotes 2 or 3;
m denotes 1;
x denotes $NR^2$ or O;
A denotes CO;
B denotes a double-bonded group selected from among $CH_2$—O or CH=CH;
$R^1$ denotes H, methyl or $CF_3$;
$R^2$ denotes H or methyl;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Particularly preferred compounds of formula 1 above are those wherein
n denotes 2;
m denotes 1;
X denotes NH;
A denotes CO;
B denotes a double-bonded group $CH_2$—O;
$R^1$ denotes H, methyl or $CF_3$;

optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also particularly preferred are the compounds of formula 1 above wherein
X denotes $NR^2$;

R² denotes cyclopropylmethyl, cyclopropylethyl, cyclopentylmethyl, cyclopentylethyl, cyclohexylmethyl or cycloheylethyl, preferably cyclopropylmethyl, cyclopentylmethyl or cyclohexylmethyl, particularly preferably cyclopropylmethyl;

and wherein the groups n, m, A, B and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also preferred are compounds of formula 1 wherein X denotes CH₂ and wherein the groups n, m, A, B and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also preferred are compounds of formula 1 wherein X denotes CO and wherein the groups n, m, A, B and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also preferred are compounds of formula 1 wherein X denotes O and wherein the groups n, m, A, B and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also preferred are compounds of formula 1 wherein X denotes S and wherein the groups n, m, A, B and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also preferred are compounds of formula 1 wherein X denotes NR₂ and wherein the groups n, m, A, B, R¹ and R² may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also preferred are compounds of formula 1 wherein X denotes NH and wherein the groups n, m, A, B and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Compounds of formula 1 wherein A denotes CO and B denotes CH₂—O are characterised by general formula 1.1.

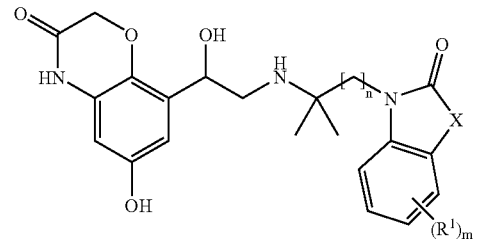

1.1

In a preferred aspect the present invention relates to compounds of formula 1.1 wherein n, m, X and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Compounds of formula 1 wherein A denotes CO and B denotes CH=CH are characterised by general formula 1.2.

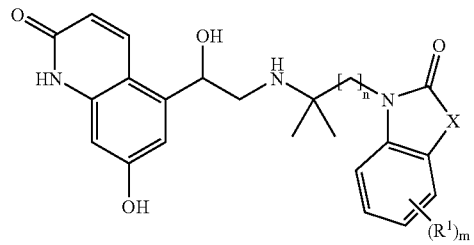

1.2

In a preferred aspect the present invention relates to compounds of formula 1.2 wherein n, m, X and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Compounds of formula 1 wherein A denotes CO and B denotes CH₂—CH₂ are characterised by general formula 1.3.

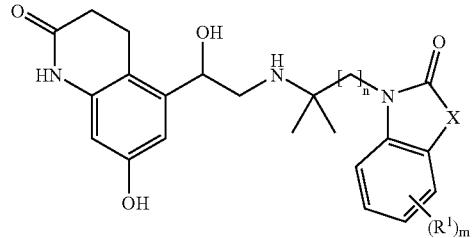

1.3

In a preferred aspect the present invention relates to compounds of formula 1.3 wherein n, m, X and R¹ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Compounds of formula 1 wherein A denotes CO and B denotes O are characterised by general formula 1.4.

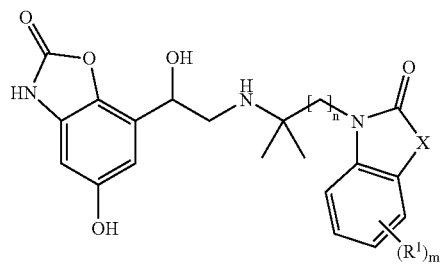

1.4

In a preferred aspect the present invention relates to compounds of formula 1.4 wherein n, m, X and $R^1$ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Compounds of formula 1 wherein A denotes CO, B denotes $CR^3R^4$—O and $R^3$ or $R^4$ denotes methyl are characterised by general formula 1.5.

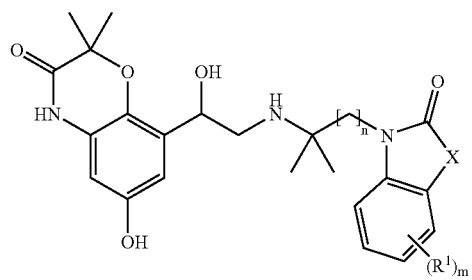

1.5

In a preferred aspect the present invention relates to compounds of formula 1.5 wherein n, m, X and $R^1$ may have the above-mentioned meanings, optionally in the form of the individual enantiomers, mixtures of the individual enantiomers or racemates, optionally in the form of the acid addition salts thereof with pharmacologically acceptable acids and optionally in the form of the solvates and/or hydrates thereof.

Also particularly preferred are compounds of formula 1, which are selected from among

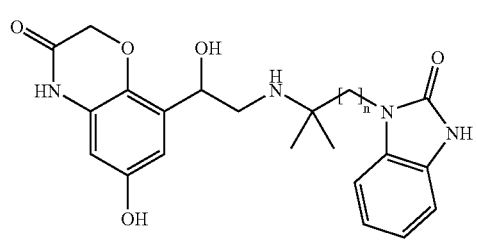

1a

-continued

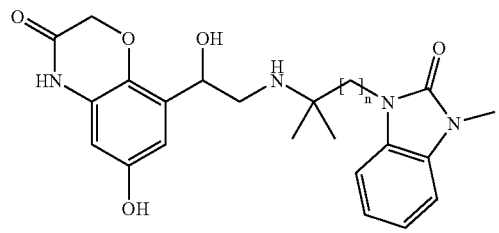

1b

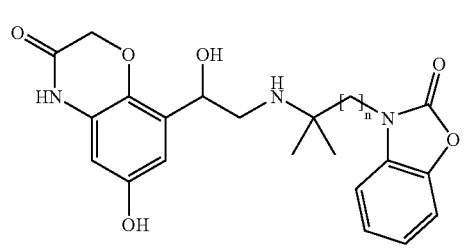

1c

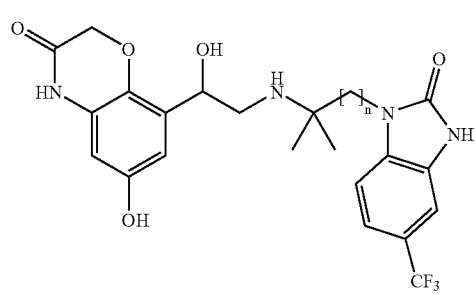

1d

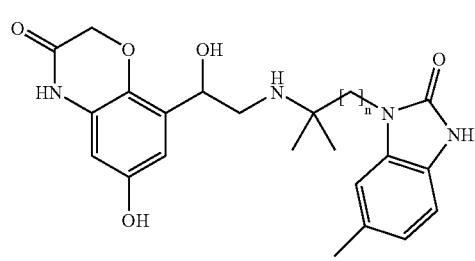

1e wherein for 1a n=2 or 3 and for 1b, 1c, 1d and 1e n=2 and the compounds are optionally in the form of the individual enantiomers, mixtures of the individual enantiomers or racemates, optionally in the form of the acid addition salts thereof with pharmacologically acceptable acids and optionally in the form of the solvates and/or hydrates thereof.

In another aspect the present invention relates to the above-mentioned new compounds of formula 1 in the form of the individual optical isomers, mixtures of the individual enantiomers or racemates. Particularly preferred are compounds of formula 1 in the form of the enantiomerically pure compounds, while the R-enantiomers of the compounds of formula 1 according to the invention are of exceptional importance. The R-enantiomers of the compounds of formula 1 may be represented by general formula R-1

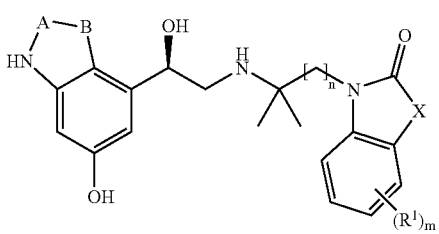

R-1 wherein the groups n, m, A, B, X and $R^1$ may have the above-mentioned meanings. Also particularly preferred of these are compounds of formula R-1, selected from among

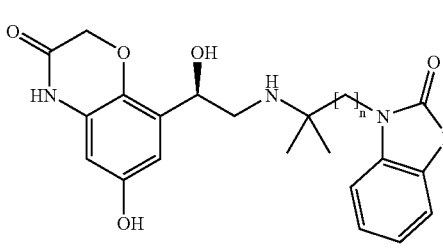

R-1a

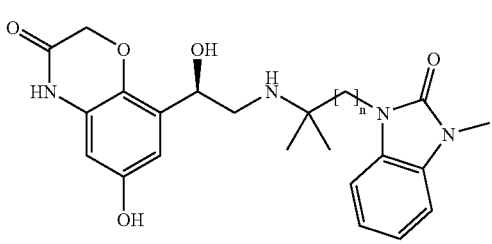

R-1b

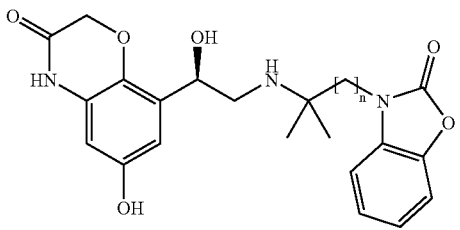

R-1c

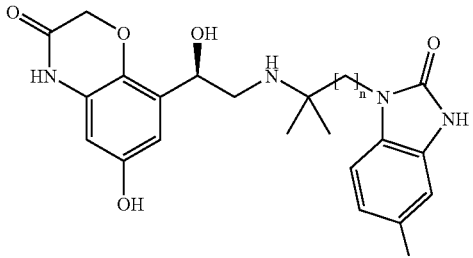

R-1d

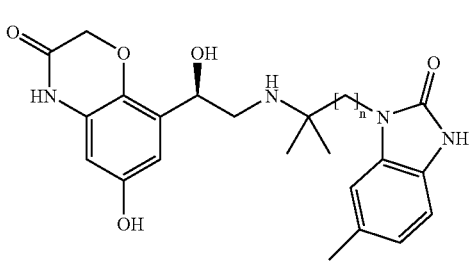

R-1e wherein in R-1a and R-1c n=2 or 3 and in R-1 b, R-1 d and R-1e n=2 and the compounds are optionally in the form of the individual enantiomers, mixtures of the individual enantiomers or racemates, optionally in the form of the acid addition salts thereof with pharmacologically acceptable acids and optionally in the form of the solvates and/or hydrates thereof.

Methods of separating racemates into the respective enantiomers are known in the art and may be used analogously to prepare the enantiomerically pure R- or S-enantiomers of the compounds of formula 1.

In another aspect the present invention relates to the above-mentioned new compounds of formula 1 as pharmaceutical compositions. The present invention further relates to the use of the above-mentioned compounds of formula 1 for preparing a pharmaceutical composition for the treatment of respiratory complaints.

The present invention preferably relates to the use of the above-mentioned compounds of formula 1 for preparing a pharmaceutical composition for the treatment of respiratory complaints selected from the group comprising obstructive pulmonary diseases of various origins, pulmonary emphysema of various origins, restrictive pulmonary diseases, interstitial pulmonary diseases, cystic fibrosis, bronchitis of various origins, bronchiectasis, ARDS (adult respiratory distress syndrome) and all forms of pulmonary oedema.

Preferably the compounds of formula 1 are used to prepare a pharmaceutical composition for the treatment of obstructive pulmonary diseases selected from among COPD (chronic obstructive pulmonary disease), bronchial asthma, paediatric asthma, severe asthma, acute asthma attacks and chronic bronchitis, while it is particularly preferable according to the invention to use them for preparing a pharmaceutical composition for the treatment of bronchial asthma.

Preferably the compounds of formula 1 are used to prepare a pharmaceutical composition for the treatment of pulmonary emphysema which has its origins in COPD (chronic obstructive pulmonary disease) or α1-proteinase inhibitor deficiency.

Preferably also, the compounds of formula 1 are used to prepare a pharmaceutical composition for the treatment of restrictive pulmonary diseases selected from among allergic alveolitis, restrictive pulmonary diseases triggered by work-related noxious substances, such as asbestosis or silicosis, and restriction caused by lung tumours, such as for example lymphangiosis carcinomatosa, bronchoalveolar carcinoma and lymphomas.

Preferably also, the compounds of formula 1 are used to prepare a pharmaceutical composition for the treatment of interstitial pulmonary diseases selected from among pneumonia caused by infections, such as for example infection by viruses, bacteria, fungi, protozoa, helminths or other pathogens, pneumonitis caused by various factors, such as for example aspiration and left heart insufficiency, radiation-induced pneumonitis or fibrosis, collagenoses, such as for example lupus erythematodes, systemic sclerodermy or sarcoidosis, granulomatoses, such as for example Boeck's disease, idiopathic interstitial pneumonia or idiopathic pulmonary fibrosis (IPF).

Preferably also, the compounds of formula 1 are used to prepare a pharmaceutical composition for the treatment of cystic fibrosis or mucoviscidosis.

Preferably also, the compounds of formula 1 are used to prepare a pharmaceutical composition for the treatment of bronchitis, such as for example bronchitis caused by bacterial or viral infection, allergic bronchitis and toxic bronchitis.

Preferably also, the compounds of formula 1 are used to prepare a pharmaceutical composition for the treatment of bronchiectasis.

Preferably also, the compounds of formula 1 are used to prepare a pharmaceutical composition for the treatment of ARDS (adult respiratory distress syndrome).

Preferably also, the compounds of formula 1 are used to prepare a pharmaceutical composition for the treatment of pulmonary oedema, for example toxic pulmonary oedema after aspiration or inhalation of toxic substances and foreign substances.

Particularly preferably the present invention relates to the use of the compounds of formula 1 for preparing a pharmaceutical composition for the treatment of asthma or COPD. Also of particular importance is the above-mentioned use of compounds of formula 1 for preparing a pharmaceutical composition for once-a-day treatment of inflammatory and obstructive respiratory complaints, particularly for the once-a-day treatment of asthma or COPD.

The present invention also relates to a process for the treatment of the above-mentioned diseases, characterised in that one or more of the above-mentioned compounds of general formula 1 are administered in therapeutically effective amounts. The present invention further relates to processes for the treatment of asthma or COPD, characterised in that one or more of the above-mentioned compounds of general formula 1 are administered once a day in therapeutically effective amounts.

In another aspect the present invention relates to the above-mentioned compounds of formula 1 in the form of the acid addition salts thereof with pharmacologically acceptable acids and optionally in the form of the solvates and/or hydrates thereof.

By acid addition salts with pharmacologically acceptable acids are meant for example salts selected from the group comprising the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, isobutyl, sec-butyl, tert-butyl, n-pentyl, isopentyl, neopentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

Alkylene groups within the scope of the present invention are bridging alkyl groups, i.e. alkyl groups linked to two other groups.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Preferred are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

The term "$C_{2-6}$-alkynyl" (including those which are part of other groups) denotes branched and unbranched alkynyl groups with 2 to 6 carbon atoms and the term "$C_{2-4}$-alkynyl" denotes branched and unbranched alkynyl groups with 2 to 4 carbon atoms, provided that they have at least one triple bond. Preferred are alkynyl groups with 2 to 4 carbon atoms. Examples include: ethynyl, propynyl, butynyl, pentynyl or hexynyl. Unless otherwise stated, the definitions propynyl, butynyl, pentynyl and hexynyl include all possible isomeric forms of the groups in question. Thus, for example, propynyl includes 1-propynyl and 2-propynyl, butynyl includes 1-, 2- and 3-butynyl, 1-methyl-1-propynyl, 1-methyl-2-propynyl etc.

The term "$C_{3-6}$-cycloalkyl" (including those which are part of other groups) denotes cyclic alkyl groups with 3 to 6 carbon atoms. Examples include: cyclopropyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine. Alkylenecycloalkyl groups are cycloalkyls linked by an alkylene bridge. These include in particular cyclopropylmethyl.

The term "$C_{1-6}$-haloalkyl" (including those which are part of other groups) denotes branched and unbranched alkyl groups with 1 to 6 carbon atoms substituted by one or more halogen atoms. By the term "$C_{1-4}$-alkyl" is meant branched and unbranched alkyl groups with 1 to 4 carbon atoms which are substituted by one or more halogen atoms. Alkyl groups with 1 to 4 carbon atoms are preferred.

Preferred halogen atoms are fluorine, chlorine, particularly preferably fluorine. Examples include: $CF_3$, $CHF_2$, $CH_2F$, $CH_2CF_3$.

The term "$C_{6-10}$-aryl" (including those which are part of other groups) denotes aromatic ring systems which may contain 6 to 10 carbon centres. Examples include: phenyl or naphthyl. Alkylene-aryl groups are aryl groups linked by an alkylene bridge. These include in particular benzyl.

Halogen within the scope of the present invention denotes fluorine, chlorine, bromine or iodine. Unless stated otherwise, fluorine, chlorine and bromine are the preferred halogens.

Compounds of general formula 1 may have acid groups, predominantly carboxyl groups, and/or basic groups such as e.g. amino functions. Compounds of general formula 1 may therefore be in the form of internal salts, salts with pharmaceutically acceptable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically acceptable bases such as alkali or alkaline earth metal hydroxides or carbonates, zinc or ammonium hydroxides or organic amines such as e.g. diethylamine, triethylamine, triethanolamine etc.

As stated previously, the compounds of formula 1 may be converted into the salts thereof, particularly, for pharmaceutical use, into the physiologically and pharmacologically acceptable salts thereof. These salts may be present on the one hand as physiologically and pharmacologically acceptable acid addition salts of the compounds of formula 1 with inorganic or organic acids. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. Mixtures of these acids may also be used. In order to prepare the alkali and alkaline earth metal salts of the compound of formula 1 it is preferable to use the alkali and alkaline earth metal hydroxides and hydrides, while the hydroxides and hydrides of the alkali metals, particularly sodium and potassium, are preferred, sodium and potassium hydroxide being particularly preferred.

If desired, the compounds of general formula (1) may be converted into the salts thereof, particularly, for pharmaceutical use, into the pharmacologically acceptable salts thereof with an inorganic or organic acid. Suitable acids for this purpose include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. Mixtures of these acids may also be used.

The invention relates to the compounds in question, optionally in the form of the individual optical isomers, mixtures of the individual enantiomers or racemates, in the form of the tautomers and in the form of the free bases or corresponding acid addition salts with pharmacologically acceptable acids—such as for example acid addition salts with hydrohalic acids—for example hydrochloric or hydrobromic acid or organic acids—such as for example oxalic, fumaric, diglycolic or methanesulphonic acid.

The compounds according to the invention may be in the form of racemates, but may also be obtained as pure enantiomers, i.e. in the (R) or (S) form. Compounds in the form of racemates or in the (R) form are preferred.

The compounds according to the invention may be prepared analogously to methods already known in the art. Suitable methods of production are known for example from U.S. Pat. Nos. 4,460,581 and 4,154,829, the whole of which is hereby incorporated by reference.

The following Examples serve to further illustrate and clarify the present invention without restricting its subject matter to the Examples provided by way of illustration.

EXAMPLES

Synthesis of Intermediates

Intermediate 1: tert-butyl (3-amino-3-methyl-butyl)-carbamate 23.6 g (117 mmol) tert-butyl (1,1-dimethyl-3-oxo-propyl)-carbamate in 700 mL ethanolic ammonia solution are treated in the presence of 3.5 g Raney nickel at ambient temperature with 3 bar hydrogen pressure until no more educt can be detected by thin layer chromatography. The catalyst is filtered off and the solvent eliminated by distillation. Dark green oil. Yield: 22.7 g (96%); mass spectroscopy: $[M+H]^+=203$.

Intermediate 2: 1-(3-amino-1,1-dimethyl-propyl)-6-methyl-1,3-dihydro-benzimidazol-2-one

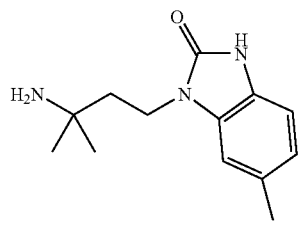

a) tert-butyl [3-methyl-3-(5-methyl-2-nitro-phenylamino)-butyl]-carbamate 2.0 g (12.9 mmol) 3-fluoro-4-nitro-toluene, 2.6 g (13.0 mmol) tert-butyl (3-amino-3-methyl-butyl)-carbamate and 2.3 g (16.8 mmol) potassium carbonate are stirred overnight at ambient temperature in 20 mL DMF. The solvent is distilled off and the residue is combined with ethyl acetate. The mixture is washed repeatedly with water, dried with sodium sulphate and the solvent is eliminated. 4.8 g yellow oil. Mass spectroscopy: $[M+H]^+=338$.

b) tert-butyl [3-(2-amino-5-methyl-phenylamino)-3-methyl-butyl]-carbamate 4.71 g (14.0 mmol) tert-butyl [3-methyl-3-(5-methyl-2-nitro-phenylamino)-butyl]-carbamate are dissolved in 110 mL methanol and hydrogenated in the presence of 340 mg palladium on charcoal (10%) at ambient temperature. Then the catalyst is separated off and the solvent is distilled off. Brown solid. Yield: 3.72 g (87%); mass spectroscopy: $[M+H]^+=308$.

c) tert-butyl [3-methyl-3-(6-methyl-2-oxo-2,3-dihydro-benzimidazol-1-yl)-butyl]-carbamate 1.76 g (5.7 mmol) tert-butyl [3-(2-amino-5-methyl-phenylamino)-3-methyl-butyl]-carbamate are dissolved in 35 mL THF, combined with 2.1 g (12.7 mmol) 1,1'-carbonyldi-(1,2,4-triazole) and stirred overnight. The solvent is distilled off and the residue is dissolved in ethyl acetate. The solution is washed successively with potassium hydrogen sulphate solution and sodium chloride solution and dried with sodium sulphate. The residue is chromatographed (silica gel; dichloromethane with 0-16% methanol:ammonia=9:1) and the crude product thus obtained is stirred with diethyl ether. Light yellow solid.
Yield: 1.12 g (59%); mass spectroscopy: $[M+H]^+=334$.

d) 1-(3-amino-1,1-dimethyl-propyl)-6-methyl-1,3-dihydro-benzimidazol-2-one

A solution of 1.50 g (4.5 mmol) tert-butyl [3-methyl-3-(6-methyl-2-oxo-2,3-dihydro-benzimidazol-1-yl)-butyl]-carbamate in 100 mL dioxane is combined with 10 mL 4 molar hydrochloric acid in dioxane and then heated to 90° C. for 90 minutes, during which time a white precipitate settles out. After cooling to ambient temperature the solvent is distilled off and the residue is stirred in diethyl ether. White solid. Yield: 1.04 g (86%; hydrochloride); mass spectroscopy: $[M+H]^+=234$.

Intermediate 3: 1-(3-amino-3-methyl-butyl)-5-trifluoromethyl-1,3-dihydro-benzimidazol-2-one

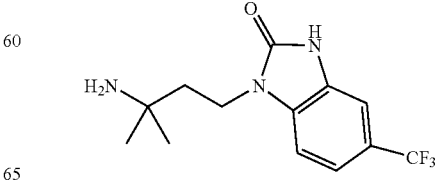

a) tert-butyl [3-methyl-3-(2-nitro-4-trifluoromethyl-phenylamino)-butyl]-carbamate This is prepared analogously to method 2a) from a total of 3.25 g (15.5 mmol) 1-fluoro-2-nitro-4-trifluoromethyl-benzene and 2.74 g (13.5 mmol) tert-butyl (3-amino-3-methyl-butyl)-carbamate. 6.1 g yellow oil. Mass spectroscopy: $[M+H]^+=392$.

b) tert-butyl [3-(2-amino-4-trifluoromethyl-phenylamino)-1,1-dimethyl-propyl]-carbamate 6.10 g (15.6 mmol) tert-butyl [3-methyl-3-(2-nitro-4-trifluoromethyl-phenylamino)-butyl]-carbamate are hydrogenated analogously to method 2b). Yield: 5.05 g (90%); mass spectroscopy: $[M+H]^+=362$.

c) tert-butyl [1,1-dimethyl-3-(2-oxo-5-trifluoromethyl-2,3-dihydro-benzimidazol-1-yl)-propyl]-carbamate 5.00 g (13.8 mmol) tert-butyl [3-(2-amino-4-trifluoromethyl-phenylamino)-1,1-dimethyl-propyl]-carbamate and 6.73 g (41.5 mmol) 1,1'-carbonyldiimidazole are reacted and worked up analogously to method 2c). White solid. Yield: 4.18 g (78%); mass spectroscopy: $[M-H]^+=386$.

d) 1-(3-amino-3-methyl-butyl)-5-trifluoromethyl-1,3-dihydro-benzimidazol-2-one Prepared analogously to method 2d) from 2.89 g (7.5 mmol) tert-butyl [1,1-dimethyl-3-(2-oxo-5-trifluoromethyl-2,3-dihydro-benzimidazol-1-yl)-propyl]-carbamate. Yield: 1.60 g (66%); mass spectroscopy: $[M+H]^+=288$.

Intermediate 4: 3-(3-amino-3-methyl-butyl)-3H-benzoxazol-2-one

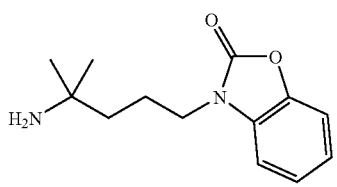

a) 1-iodo-4-methyl-nitro-pentane

A solution of 44.7 mL (352 mmol) chlorotrimethylsilane and 50 mL acetonitrile is added dropwise to 26.0 g (177 mmol) 1-methyl-4-nitro-pentan-1-ol and 52.8 g (352 mmol) sodium iodide in 350 mL acetonitrile. Then the mixture is heated to 50° C. for 4 hours, then the solvent is distilled off and the residue is combined with 500 mL diethyl ether. It is washed successively with water, sodium thiosulphate solution and sodium chloride solution. The organic phase is dried with sodium sulphate and evaporated down. 34.2 g of red oil.

b) 3-(3-methyl-3-nitro-butyl)-3H-benzoxazol-2-one 1.70 g (42.5 mmol) sodium hydride (60%) are added batchwise to a solution of 4.50 g (33.3 mmol) benzoxazol-2-one in 50 mL DMF, while the temperature is kept below 0° C. by cooling. After one hour's stirring a solution of 9.61 g (37.4 mmol) 1-iodo-4-methyl-4-nitro-pentane in 20 mL DMF is added dropwise so that the temperature does not exceed 5° C. The mixture is stirred overnight at ambient temperature and the solvent is distilled off. The residue is taken up in ethyl acetate and washed successively with water and sodium chloride solution, dried with sodium sulphate and evaporated down. 11.0 g oil are obtained. Mass spectroscopy: $[M+H]^+=265$.

c) 3-(3-amino-3-methyl-butyl)-3H-benzoxazol-2-one 11.0 g 3-(3-methyl-3-nitro-butyl)-3H-benzoxazol-2-one from the reaction described above are dissolved in 130 mL ethanol and hydrogenated with Raney nickel as catalyst at 5 bar for 20 hours. The catalyst is filtered off and the filtrate is freed from the solvent. 10% ethanolic hydrochloric acid is added, the solvent is distilled off and the residue is stirred in an acetone/diethyl ether mixture. White solid. Yield: 6.0 g (77% over 2 steps, hydrochloride); melting range=145-147° C.

Intermediate 5: 3-(3-amino-3-methyl-butyl)-3H-benzoxazol-2-one

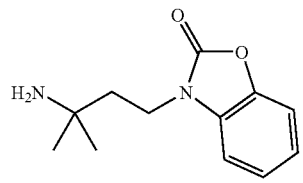

a) tert-butyl [1,1-dimethyl-3-(2-oxo-benzooxazol-3-yl)-propyl]-carbamate 4.0 g (29.6 mmol) benzoxazol-2-one are dissolved in 40 mL DMPU and cooled with an ice bath. Under protective gas 897 mg (95%; 35.5 mmol) sodium hydride are added batchwise to this solution. The reaction mixture is heated to ambient temperature and then stirred for another hour. 9.85 g (44.4 mmol) tert-butyl (3-amino-1,1-dimethyl-propyl)-carbamate and 1.97 g (5.3 mmol) tetrabutylammonium iodide are added and the mixture is stirred overnight. The reaction is stopped by the careful addition of sodium hydrogen carbonate solution. Ethyl acetate is added, the aqueous phase is separated off and extracted repeatedly with ethyl acetate. The combined organic phases are washed with sodium chloride solution, dried with sodium sulphate and evaporated down. Purification of the residue by column chromatography (silica gel; petroleum ether/ethyl acetate=7:3) yields the desired product in the form of an oil. Yield 4.1 g (43%); mass spectroscopy: $[M+H]+=321$.

b) 3-(3-amino-3-methyl-butyl)-3H-benzoxazol-2-one 18 mL trifluoroacetic acid are added dropwise at ambient temperature to a solution of 4.0 g (12.5 mmol) tert-butyl [1,1-dimethyl-3-(2-oxo-benzooxazol-3-yl)-propyl]-carbamate in 110 mL dichloromethane. The mixture is stirred overnight and then the solvent is distilled off. The oil remaining is stirred in diethyl ether, during which time a solid is precipitated, which is filtered off. After stirring again with diethyl ether and filtration a beige solid is obtained.

Yield: 3.63 g (65%; trifluoroacetate); mass spectroscopy: $[M+H]+=221$.

Intermediate 6: 5-benzyloxy-7-(2-ethoxy-2-hydroxy-acetyl)-3H-benzoxazol-2-one

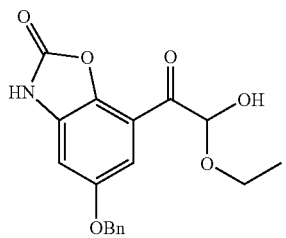

a) 1-(5-benzyloxy-2-hydroxy-3-nitro-phenyl)-ethanone 18 mL of fuming nitric acid are added dropwise to a solution of 81.5 g (0.34 mol) 1-(5-benzyloxy-2-hydroxy-phenyl)-ethanone (known from U.S. Pat. No. 4,460,581) in 700 mL acetic acid, while cooling with the ice bath, such that the temperature does not exceed 20° C. Then the reaction mixture is stirred for two hours at ambient temperature, poured onto ice water and filtered. The product is recrystallised from isopropanol, suction filtered and washed with isopropanol and diisopropylether. Yield: 69.6 g (72%); mass spectroscopy $[M+H]^+=288$.

b) 1-(3-amino-5-benzyloxy-2-hydroxy-phenyl)-ethanone 69.5 g (242 mmol) 1-(5-benzyloxy-2-hydroxy-3-nitro-phenyl)-ethanone are dissolved in 1.4 L methanol and hydrogenated in the presence of 14 g rhodium on charcoal (10%) as catalyst at 3 bar and ambient temperature. Then the catalyst is filtered off and the filtrate is evaporated down. The residue is further reacted without any additional purification.

Yield: 60.0 g (96%), $R_f$ value=0.45 (dichloromethane on silica gel).

c) 7-acetyl-5-benzyloxy-3H-benzoxazol-2-one

At 20 to 40° C. 52 g (0.53 mol) phosgene are piped into a solution of 121 g (0.47 mol) 1-(3-amino-5-benzyloxy-2-hydroxy-phenyl)-ethanone in 800 mL pyridine. The reaction mixture is heated to 50° C. for 2 hours, then poured onto ice and acidified with conc. hydrochloric acid. A reddish-brown solid is isolated which is repeatedly recrystallised from ethanol with the addition of activated charcoal.

Yield: 67.5 g (50.6%); melting range: 163-166° C.

d) 5-benzyloxy-7-(2-ethoxy-2-hydroxy-acetyl)-3H-benzoxazol-2-one 20 g (71 mmol) 7-acetyl-5-benzyloxy-3H-benzoxazol-2-one and 8 g (72 mmol) selenium dioxide are refluxed for 8 hours in the presence of activated charcoal in 100 mL dioxane and 3.1 mL water. The solid is filtered off, the solvent is distilled off and the residue is combined with 50 mL ethanol. The mixture is refluxed for 15 minutes and then filtered through activated charcoal. The solid precipitated on cooling is suction filtered after 3 hours and washed with ethanol and diethyl ether.

Yield: 7 g (29%); melting range: 140-143° C.

Intermediate 7: 6-benzyloxy-8-(2-ethoxy-2-hydroxy-acetyl)-2,2-dimethyl-4H-benzo[1,4]oxazin-3-one

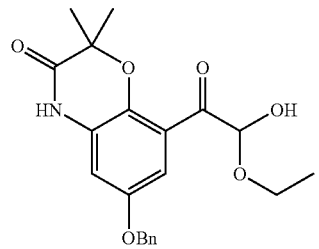

a) N-(3-acetyl-5-benzyloxy-2-hydroxy-phenyl)-2-bromo-2-methyl-propionamide 4.64 g (25 mmol) 2-bromo-2-methyl-propionyl chloride are added dropwise at 5 to 20° C. to a solution of 5.15 g (20 mmol) 1-(3-amino-5-benzyloxy-2-hydroxy-phenyl)-ethanone in 20 mL pyridine. After the addition has ended the mixture is stirred for 15 minutes, combined with ice water and 100 mL ethyl acetate and acidified with conc. hydrochloric acid. The organic phase is separated off, washed with water and dried with sodium sulphate. After the solvent has been distilled off the residue is crystallised from a diethyl ether/petroleum ether mixture.

Yield: 6.8 g (84%); melting range: 88-90° C.

b) 8-acetyl-6-benzyloxy-2,2-dimethyl-4H-benzo[1.4]oxazin-3-one 6.60 g (16.2 mmol) N-(3-acetyl-5-benzyloxy-2-hydroxy-phenyl)-2-bromo-2-methyl-propionamide and 2.76 g (20 mmol) potassium carbonate are stirred for 1 hour in 70 mL acetonitrile at reflux temperature. The solid is suction filtered, the filtrate is evaporated down and the residue is combined with 30 mL ethyl acetate. After further filtration and after the solvent has been distilled off the crude product is crystallised from a little methanol.

Yield: 1.00 g (19%); mass spectroscopy $[M+H]^+=326$; melting range: 148-150° C.

c) 6-benzyloxy-8-(2-ethoxy-2-hydroxy-acetyl)-2,2-dimethyl-4H-benzo[1,4]oxazin-3-one This is prepared analogously to the method described for Intermediate 6d from 8-acetyl-6-benzyloxy-2,2-dimethyl-4H-benzo[1,4]oxazin-3-one.

Intermediate 8: 7-benzyloxy-5-oxiranyl-1H-quinolin-2-one

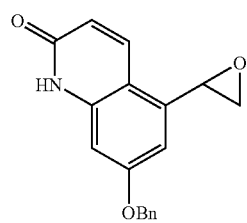

a) 2-acetyl-4-benzyloxy-6-nitro-phenyl trifluoromethanesulphonate 92.7 mL (660 mmol) triethylamine are added to 90 g (313 mmol) 1-(5-benzyloxy-2-hydroxy-3-nitro-phenyl)-ethanone in 940 mL dichloromethane at −10° C. Then a solution of 65 mL (394 mmol) trifluoromethanesulphonic acid anhydride and 40 mL dichloromethane is slowly added dropwise. After 15 minutes stirring at −5° C. the reaction is stopped by careful addition of 400 mL ammonium chloride solution and 400 mL sodium hydrogen carbonate solution. The organic phase is separated off, dried with sodium sulphate and evaporated down. The residue is dissolved in 150 mL diethyl ether and then precipitated by the addition of 800 mL hexane. The solid is filtered off, suspended in a diethyl ether/hexane mixture and suction filtered again.

Yield: 118 g (90%); mass spectroscopy: $[M+H]^+=420$.

b) methyl 3-(2-acetyl-4-benzyloxy-6-nitro-phenyl)-acrylate 5.88 g (6.42 mmol) tris-(dibenzylideneacetone)-dipalladium, 3.50 g (12.01 mmol) tri-tert-butylphosphonium tetrafluoroborate, 81.2 mL (371 mmol) dicyclohexylmethylamine, 105.8 g (286 mmol) tetrabutylammonium iodide and 32.6 mL (362 mmol) methylacrylate are added to a solution of 100 g (238 mmol) 2-acetyl-4-benzyloxy-6-nitro-phenyl trifluoromethanesulphonate in 360 mL dioxane. The reaction mixture is stirred for 2 hours at 80° C. under a nitrogen atmosphere in the presence of 100 g molecular sieve 4A and then combined with 2 L diethyl ether and 500 g silica gel. After 10 minutes the silica gel is suction filtered, while washing repeatedly with diethyl ether. The combined organic phases are washed successively with 1 N hydrochloric acid, sodium carbonate solution and sodium chloride solution. The solvent is distilled off, the residue is crystallised from ethanol and the solid is filtered off and washed with ethanol.

Yield: 32.2 g (38%); mass spectroscopy: $[M+H]^+=356$.

c) 5-acetyl-7-benzyloxy-3,4-dihydro-1H-quinolin-2-one 5.0 g (14.07 mmol) methyl 3-(2-acetyl-4-benzyloxy-6-nitro-phenyl)-acrylate are combined with 100 mL ethanol and hydrogenated at 4 bar with Raney nickel as catalyst. The catalyst is separated off and the filtrate is acidified with 15 mL 2 N hydrochloric acid. The product that crystallises out is suction filtered and dried.

Yield: 1.0 g (24%); mass spectroscopy: $[M+H]^+=296$.

d) 5-acetyl-7-benzyloxy-1H-quinolin-2-one 13.0 g (44 mmol) 5-acetyl-7-benzyloxy-3,4-dihydro-1H-quinolin-2-one are suspended in 130 mL dioxane and combined with 15.0 g (66 mmol) of 2,3-dichloro-5,6-dicyanobenzoquinone. The mixture is refluxed for 30 minutes, cooled to ambient temperature and stirred for a further 2 hours. The solid is filtered off, washed with dioxane and dissolved in 600 mL dichloromethane/methanol (9:1). The solution is washed with sodium hydrogen carbonate solution, dried with sodium sulphate and evaporated down. Then the residue is suspended in methanol, filtered and dried.

Yield: 8.3 g (64%); mass spectroscopy: $[M+H]^+=294$.

e) 7-benzyloxy-5-(2-chloro-acetyl)-1H-quinolin-2-one 7.0 g (23.9 mmol) 5-acetyl-7-benzyloxy-1H-quinolin-2-one and 19.0 g (54.6 mmol) benzyltrimethylammonium dichloriodate are stirred in 43 mL acetic acid, 7 mL water and 147 mL dichloroethane at 65° C. After 4.5 hours the raction is stopped by the addition of 400 mL sodium carbonate solution and 50 mL 5% sodium sulphite solution. The insoluble constituents are suction filtered, washed with water and dried.

Yield: 6.0 g (77%); mass spectroscopy: $[M+H]^+=328$.

f) 7-benzyloxy-5-oxiranyl-1H-quinolin-2-one 6.0 g (18.3 mmol) 7-benzyloxy-5-(2-chloro-acetyl)-1H-quinolin-2-one are placed in 150 mL tetrahydrofuran and at 0 to 5° C. combined with 434 mg (19.9 mmol) lithium borohydride. The mixture is stirred for 30 minutes, then 43 mL of a 2.5 molar sodium hydroxide solution are added and the mixture is stirred for a further 4 hours wwhile being heated to ambient temperature. The mixture is combined with sodium chloride solution, filtered and extracted repeatedly with ethyl acetate/tetrahydrofuran (1:1). The filtered-off solid and the organic phases are combined and freed from the solvent. The residue is suspended in methanol, suction filtered and dried.

Yield 4.8 g (89%); mass spectroscopy: $[M+H]^+=294$.

Intermediate 9:1-(3-amino-3-methyl-butyl)-4-methoxy-1,3-dihydro-benzimidazol-2-one

a) 4-methyl-4-nitro-pentan-1-ol 50 g (0.285 mol) methyl 4-methyl-4-nitro-pentanoate are dissolved in a 6:4 mixture of THF/ethanol (1000 mL). The solution is cooled to −10° C. and combined with 24.2 g (0.571 mol) lithium chloride. Then 21.6 g (0.571 mol) lithium borohydride are added batchwise. The mixture is stirred for 30 minutes at −10° C. and then heated overnight to ambient temperature. The reaction mixture is stirred for 6 hours at 60° C. and overnight at ambient temperature. It is combined with water and adjusted to pH 6 with dilute hydrochloric acid. The solvent is distilled off and the residue is combined with water. The mixture is extracted with dichloromethane, the combined organic phases are washed with water and ammonium chloride solution and dried with sodium sulphate. After elimination of the solvent the product is obtained as a yellow oil.

Yield: 40.0 g (95%); mass spectroscopy: $[M+H]^+=148$.

b) 1-iodo-4-methyl-4-nitro-pentane 70 mL (0.544 mol) trimethylchlorosilane are added dropwise at ambient temperature to 40 g (0.272 mol) 4-methyl-4-nitro-pentan-1-ol and 81.5 g (0.544 mol) sodium iodide in 350 mL acetonitrile. The reaction mixture is filtered, evaporated down and combined with diethyl ether. The organic phase is washed with sodium bisulphite solution and water, dried and freed from the solvent. Yellow oil.

Yield: 56.0 g (80%); mass spectroscopy: $[M-NO_2]^+=211$.

c) 2-methoxy-6-nitro-phenylamine

85% potassium hydroxide solution (11.7 g, 0.179 mol) is added to a solution of 25 g (0.162 mol) 2-amino-3-nitro-phenol in 200 mL DMF. Then 11.1 mL (0.178 mol) iodomethane are added dropwise and the mixture is stirred overnight at ambient temperature. The reaction mixture is poured onto ice and stirred for one hour. The precipitated product is filtered off, washed with water and dried.

Yield: 23.8 g (87%); mass spectroscopy: $[M+H]^+=169$.

d) ethyl (2-methoxy-6-nitro-phenyl)-carbamate 17.1 mL (0.141 mol) trichloromethylchloroformate are added dropwise at reflux temperature to a solution of 23.8 g (0.142 mol) 2-methoxy-6-nitro-phenylamine in 300 mL THF and then the mixture is stirred for 4 hours at this temperature. The solvent is distilled off and the residue is stirred with isopropanol, during which time a yellow solid is precipitated. Yield: 25.0 g (73%); mass spectroscopy: $[M+H]^+=241$.

e) ethyl (2-amino-6-methoxy-phenyl)-carbamate 25.0 g (0.104 mol) ethyl (2-methoxy-6-nitro-phenyl)-carbamate are dissolved in 400 mL methanol. 116.4 g (0.516 mol) $SnCl_2\ 2H_2O$ are added and the mixture is refluxed for 3 hours. The reaction mixture is evaporated down, combined with sodium carbonate solution and filtered. The aqueous phase is repeatedly extracted with dichloromethane and the combined organic phases are washed with sodium chloride solution, dried and evaporated down. The residue that crystallises out on standing is stirred with isopropanol. Yield: 13.0 g (59%); mass spectroscopy: $[M+H]^+=211$.

f) ethyl 7-methoxy-2-oxo-2,3-dihydro-benzimidazol-1-carboxylate 13.0 g (0.062 mol) ethyl (2-amino-6-methoxy-phenyl)-carbamate and 10.3 mL (0.074 mol) triethylamine in 100 mL dichloromethane are added to a solution of 8.20 mL (0.068 mol) trichloromethylchloroformate in 50 mL dichloromethane while cooling with ice. After 4 hours stirring at ambient temperature the reaction mixture is poured onto ice and extracted with dichloromethane. The combined organic phases are washed with water, dried and freed from the solvent. The residue is stirred in diethyl ether.

Yield: 9.0 g (62%); mass spectroscopy: $[M+H]^+=237$.

g) 4-methoxy-1-(3-methyl-3-nitro-butyl)-1,3-dihydro-benzimidazol-2-one 4.0 g (17 mmol) ethyl 7-methoxy-2-oxo-2,3-dihydro-benzimidazol-1-carboxylate in DMF are combined with 85% potassium hydroxide solution (3.3 g, 51 mmol) while being cooled with the ice bath. After 30 minutes a solution of 5.2 g (21 mmol) 1-iodo-4-methyl-4-nitro-pentane in DMF is added and the mixture is stirred overnight at ambient temperature. The reaction mixture is diluted with water and extracted with ethyl acetate. The combined organic phases are washed with water, dried and freed from the solvent. The oil remaining is purified by chromatography on a silica gel column (cyclohexane/ethyl acetate gradient). Yield: 0.5 g (8%); mass spectroscopy: $[M+H]^+=366$.

h) 1-(3-amino-3-methyl-butyl)-4-methoxy-1,3-dihydro-benzimidazol-2-one 1.4 g (4.8 mmol) 4-methoxy-1-(3-methyl-3-nitro-butyl)-1,3-dihydro-benzimidazol-2-one are dissolved in methanol and hydrogenated at 3 bar in the presence of Raney nickel. The catalyst is separated off, the solvent is distilled off and the residue is dissolved in ethanolic hydrochloric acid. The solvents are eliminated by distillation and the solid remaining is stirred with isopropanol.

Yield: 0.6 g (42%, hydrochloride); mass spectroscopy: $[M+H]^+=300$.

Intermediate 10: 1-(3-amino-3-methyl-butyl)-5-methoxy-3-methyl-1,3-dihydro-benzimidazol-2-one

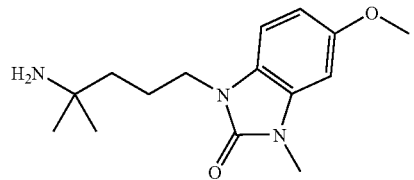

a) (5-methoxy-2-nitro-phenyl)-methyl-amine 83.5 mL (167.0 mmol) of a 2 molar solution of methylamine in THF are added dropwise to 14.3 g (83.56 mmol) 3-fluoro-4-nitro-anisol and 12.71 g (92.02 mmol) potassium carbonate in 200 mL dichloromethane. The mixture is stirred overnight and then combined with water. The organic phase is washed successively with water and ammonium chloride solution, dried and evaporated down. The yellow solid remaining is stirred with hexane. Yield: 12.7 g (84%); mass spectroscopy: $[M+H]^+=183$.

b) 4-methoxy-N-2-methyl-benzene-1,2-diamine 12.5 g (68.6 mmol) (5-methoxy-2-nitro-phenyl)-methyl-amine and 77.39 g (343.0 mmol) $SnCl_2\ 2H_2O$ in 200 mL ethanol are refluxed for 6 hours. The reaction mixture is washed with sodium carbonate solution, filtered and evaporated down. The residue is combined with water and extracted with ethyl acetate. The combined organic phases are washed with water, dried and freed from the solvent. Oil.

Yield: 8.0 g (77%); mass spectroscopy: $[M+H]^+=153$.

c) 5-methoxy-1-methyl-1,3-dihydro-benzimidazol-2-one 8.0 g (52.56 mmol) 4-methoxy-N-2-methyl-benzene-1,2-diamine and 8.7 mL (63.00 mmol) triethylamine are dissolved in 100 mL dichloromethane and added dropwise to 7 mL (58.00 mmol) trichloromethylchloroformate in 50 mL dichloromethane. The reaction mixture is stirred overnight at ambient temperature, then poured into ice water and extracted with dichloromethane. The combined organic phases are washed with water, dried and evaporated down. The remaining solid is stirred with diethyl ether.

Yield: 4.2 g (45%); mass spectroscopy: $[M+H]^+=179$.

d) 5-methoxy-3-methyl-1-(3-methyl-3-nitro-butyl)-1,3-dihydro-benzimidazol-2-one 1.1 g (28 mmol) 60% sodium hydride are added to 2.5 g (14 mmol) 5-methoxy-1-methyl-1,3-dihydro-benzimidazol-2-one in 30 mL DMF while being cooled with the ice bath. After 30 minutes a solution of 1-iodo-4-methyl-4-nitro-pentane in 20 mL DMF is piped in and the mixture is stirred overnight. It is diluted with water and extracted with ethyl acetate. The combined organic phases are washed with water, dried and evaporated down. The solid remaining is stirred with diethyl ether.

Yield: 2.7 g (63%); mass spectroscopy: [M+H]$^+$=308.

e) 1-(3-amino-3-methyl-butyl)-5-methoxy-3-methyl-1,3-dihydro-benzimidazol-2-one 2.7 g (8.7 mmol) 5-methoxy-3-methyl-1-(3-methyl-3-nitro-butyl)-1,3-dihydro-benzimidazol-2-one and 9.93 g (44.0 mmol) SnCl$_2$ 2H$_2$O in 200 mL ethanol are refluxed for 3 hours. The reaction mixture is evaporated down, combined with sodium carbonate solution and filtered. The filtrate is extracted with ethyl acetate and the combined organic phases are washed with water, dried and freed from the solvent. The residue is dissolved in ethanol and the solution is combined with ethereal hydrochloric acid. After the solvent has been distilled off the solid remaining is stirred with diisopropylether.

Yield: 0.7 g (29%); mass spectroscopy: [M+H]$^+$=278.

Intermediate 11: 3-(4-amino-4-methyl-pentyl)-5-fluoro-1-methyl-1,3-dihydro-benzimidazol-2-one

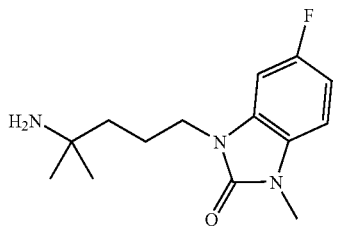

a) (4-fluoro-2-nitro-phenyl)-methyl-amine 157 ml (314 mmol) of a 2 molar solution of methylamine in THF are added dropwise, with cooling, to 25 g (157 mmol) 2,4-difluoro-nitrobenzene and 23.9 g (173 mmol) potassium carbonate in 300 mL dichloromethane. The mixture is stirred overnight at ambient temperature and then combined with water. The organic phase is washed with water, dried and evaporated down. The residue is stirred with diethyl ether.

Yield: 18 g (69%); mass spectroscopy [M+H]$^+$=171.

b) 4-fluoro-N-1-methyl-benzene-1,2-diamine 22 g (0.12 mol) (4-fluoro-2-nitro-phenyl)-methyl-amine in 250 mL ethanol are hydrogenated at 4 bar hydrogen pressure with palladium on charcoal as catalyst. The catalyst is separated off and the solvent is distilled off. The oil remaining is purified by chromatography (silica gel, hexane/ethyl acetate gradient). The product is obtained in the form of an oil.

Yield: 9 g (50%); mass spectroscopy [M+H]$^+$=141.

c) 5-fluoro-1-methyl-1,3-dihydro-benzimidazol-2-one 13.0 g (92.1 mmol) 4-fluoro-N-1-methyl-benzene-1,2-diamine are reacted with trichloromethyl chloroformate analogously to the method described for the intermediate 10c. After stirring in diethyl ether the product is isolated as a solid.

Yield: 6.0 g (39%); mass spectroscopy: [M+H]$^+$=167.

d) 5-fluoro-1-methyl-3-(4-methyl-4-nitro-pentyl)-1,3-dihydro-benzimidazol-2-one

First of all 0.624 g (13.9 mmol) 60% sodium hydride and then, with cooling, 4.6 g (17.8 mmol) 1-iodo-4-methyl-4-nitro-pentane in 10 mL DMF are added to a solution of 2.1 g (12.6 mmol) 5-fluoro-1-methyl-1,3-dihydro-benzimidazol-2-one in DMF. The reaction mixture is stirred overnight at ambient temperature, then poured onto water and extracted with diethyl ether. The organic phases are evaporated down and the residue is recrystallised from isopropylether. Yield: 1.8 g (48%); mass spectroscopy [M+H]$^+$=296.

e) 3-(4-amino-4-methyl-pentyl)-5-fluoro-1-methyl-1,3-dihydro-benzimidazol-2-one 1.8 g (6.09 mmol) 5-fluoro-1-methyl-3-(4-methyl-4-nitro-pentyl)-1,3-dihydro-benzimidazol-2-one in 50 mL methanol are hydrogenated at 3 bar hydrogen pressure with Raney nickel as catalyst. The catalyst is separated off and the solvent is distilled off. In order to prepare the hydrochloride the residue is combined with ethanol and hydrochloric acid in diethyl ether.

Yield: 1.5 g (83%, hydrochloride); melting range=225-228° C.; mass spectroscopy [M+H]$^+$=303.

Intermediate 12: 3-(4-amino-4-methyl-pentyl)-4-fluoro-1-methyl-1,3-dihydro-benzimidazol-2-one

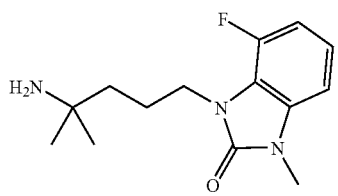

a) (3-fluoro-2-nitro-phenyl)-methyl-amine

Reaction of 2.0 g (2.6 mmol) 2,6-difluoro-nitrobenzene with a 2 molar solution of methylamine in THF analogously to the process for preparing Intermediate 10a. Red solid. Yield: 1.8 g (86%); mass spectroscopy: [M+H]$^+$=171.

b) 3-fluoro-N-1-methyl-benzene-1,2-diamine

Reduction of 8.0 g (47.0 mmol) (3-fluoro-2-nitro-phenyl)-methyl-amine with SnCl$_2$×2H$_2$O according to the method described for Intermediate 10b. Red oil.

Yield: 4.5 g (68%); mass spectroscopy: [M+H]$^+$=141.

c) 4-fluoro-1-methyl-1,3-dihydro-benzimidazol-2-one

Prepared from 4.5 g (32.1 mmol) 3-fluoro-N-1-methyl-benzene-1,2-diamine analogously to the method described for Intermediate 10c. Brown solid. Yield: 1.4 g (26%); mass spectroscopy: [M+H]$^+$=167.

d) 4-fluoro-1-methyl-3-(4-methyl-4-nitro-pentyl)-1,3-dihydro-benzimidazol-2-one

Prepared from 1.4 g (8.42 mmol) 4-fluoro-1-methyl-1,3-dihydro-benzimidazol-2-one analogously to the method for preparing Intermediate 10d. Yellow oil.

Yield: 1.7 g (68%); mass spectroscopy: [M+H]$^+$=296.

e) 3-(4-amino-4-methyl-pentyl)-4-fluoro-1-methyl-1,3-dihydro-benzimidazol-2-one

A solution of 2 g (6.7 mmol) 4-fluoro-1-methyl-3-(4-methyl-4-nitro-pentyl)-1,3-dihydro-benzimidazol-2-one in methanol is hydrogenated at 3 bar hydrogen pressure in the presence of Raney nickel. After separation of the catalyst hydrochloric acid in diethyl ether is added. The hydrochloride precipitated is filtered off and dried. Yield: 1.5 g (83%, hydrochloride); melting range=230-232° C.; mass spectroscopy: [M+H]$^+$=303.

Synthesis of End Compounds

General Method 1:

1 mmol of glyoxalaldehyde or -acetal and 1 mmol amine are stirred for 30 minutes in 5 mL tetrahydrofuran at 50° C. The mixture is cooled to 0° C. and under an argon atmosphere 1.5 mL of a 2 molar solution of lithium borohydride in tetrahydrofuran is added dropwise. The mixture is stirred for 30 min at 0° C., combined with 10 mL dichloromethane and 3 mL water, stirred for a further hour at ambient temperature and then filtered through kieselguhr, eluting with dichloromethane. The eluate is freed from the solvent and the residue is purified by chromatography if necessary. The benzylether thus obtained is dissolved in methanol and hydrogenated with palladium on charcoal (10%) as catalyst at 2.5 bar and ambient temperature. Then the catalyst is separated off and the crude product is purified by chromatography (reverse phase, acetonitrile/water gradient with 0.1% trifluoroacetic acid) or crystallised in acetonitrile.

General Method 2

1 mmol glyoxalaldehyde or -acetal and 1 mmol amine are suspended in 5 mL ethanol and heated to 70° C. The solution formed is stirred for one hour at 70° C. and then cooled to ambient temperature. After the addition of 113 mg (3 mmol) sodium borohydride the mixture is stirred for 3 hours at ambient temperature, combined with 0.7 mL saturated potassium carbonate solution and stirred for a further 30 minutes. The mixture is filtered through aluminium oxide (basic), repeatedly washed with dichloromethane/methanol 15:1, evaporated down and chromatographed (silica gel; dichloromethane with 0-10% methanol:ammonia=9:1). The benzyl compound thus obtained is dissolved in 10 mL methanol and hydrogenated with palladium on charcoal as catalyst at 1 bar hydrogen pressure. Then the catalyst is filtered off and the filtrate is evaporated down.

Example 1

8-{2-[1,1-dimethyl-3-(6-methyl-2-oxo-2,3-dihydro-benzimidazol-1-yl)-propylamino]-1-hydroxy-ethyl}-6-hydroxy-4H-benzo[1,4]oxazin-3-one

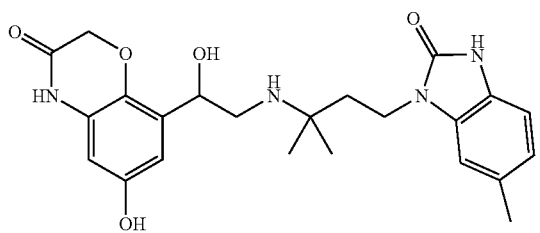

The compound is prepared according to general method 1 from 357 mg (1 mmol) 6-benzyloxy-8-(2-ethoxy-1,2-dihydroxy-ethyl)-4H-benzo[1,4]oxazin-3-one and 233 mg (1 mmol) 1-(3-amino-3-methyl-butyl)-6-methyl-1,3-dihydro-benzimidazol-2-one. Yield: 170 mg (31%, trifluoroacetate); mass spectroscopy: [M+H]$^+$=441.

Example 2

8-{2-[1,1-dimethyl-3-(2-oxo-5-trifluoromethyl-2,3-dihydro-benzimidazol-1-yl)-propylamino]-1-hydroxy-ethyl}-6-hydroxy-4H-benzo[1,4]oxazin-3-one

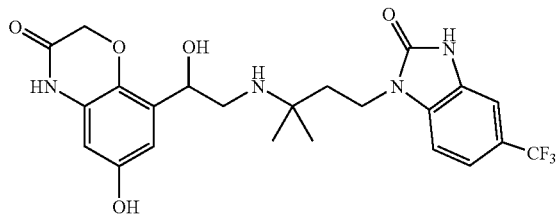

Prepared according to general method 1 from 357 mg (1 mmol) 6-benzyloxy-8-(2-ethoxy-1,2-dihydroxy-ethyl)-4H-benzo[1,4]oxazin-3-one and 287 mg (1 mmol) 1-(3-amino-3-methyl-butyl)-5-trifluoromethyl-1,3-dihydro-benzimidazol-2-one. Yield: 76 mg (13%, trifluoroacetate); mass spectroscopy: [M+H]$^+$=495.

Example 3

8-[2-[1,1-dimethyl-4-(2-oxo-benzooxazol-3-yl)-butylamino]-1-hydroxy-ethyl]-6-hydroxy-4H-benzo[1,4]oxazin-3-one

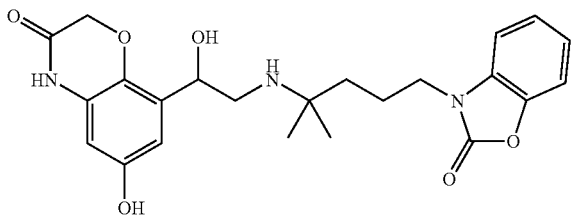

357 mg (1 mmol) 6-benzyloxy-8-(2-ethoxy-1,2-dihydroxy-ethyl)-4H-benzo[1,4]oxazin-3-one and 287 mg (1 mmol) 3-(4-amino-4-methyl-pentyl)-3H-benzoxazol-2-one are reacted according to general method 1. After hydrogenolytic cleaving of the benzyl protecting group an oil is isolated from which the product is obtained by stirring in an acetone/diethyl ether mixture. Yield: 161 mg (29%, trifluoroacetate); mass spectroscopy: [M+H]$^+$=442.

Example 4

8-[2-[1,1-dimethyl-3-(3-methyl-2-oxo-2,3-dihydro-benzimidazol-1-yl)-propylamino]-1-hydroxy-ethyl]-6-hydroxy-4H-benzo[1,4]oxazin-3-one

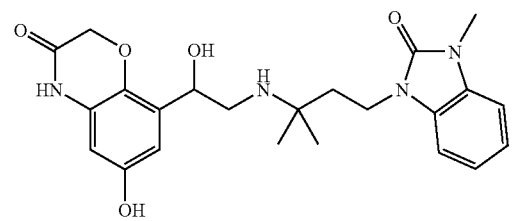

Prepared according to general method 2 from 357 mg (1 mmol) 6-benzyloxy-8-(2-ethoxy-1,2-dihydroxy-ethyl)-4H-benzo[1,4]oxazin-3-one and 233 mg (1 mmol) 1-(3-amino-3-methyl-butyl)-3-methyl-1,3-dihydro-benzimidazol-2-one.

Yield: 270 mg (61%); mass spectroscopy: [M+H]$^+$=441.

Example 5

8-{2-[1,1-dimethyl-3-(2-oxo-2,3-dihydro-benzimidazol-1-yl)-propylamino]-1-hydroxy-ethyl}-6-hydroxy-4H-benzo[1,4]oxazin-3-one

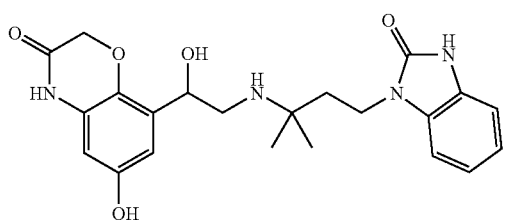

The target compound is obtained according to general method 2 from 357 mg (1 mmol) 6-benzyloxy-8-(2-ethoxy-1,2-dihydroxy-ethyl)-4H-benzo[1,4]oxazin-3-one and 219 mg (1 mmol) 1-(3-amino-3-methyl-butyl)-1,3-dihydro-benzimidazol-2-one. Yield: 187 mg (44%); mass spectroscopy: [M+H]$^+$=427.

Example 6

8-{2-[1,1-dimethyl-4-(2-oxo-2,3-dihydro-benzimidazol-1-yl)-butylamino]-1-hydroxy-ethyl}-6-hydroxy-4H-benzo[1,4]oxazin-3-one

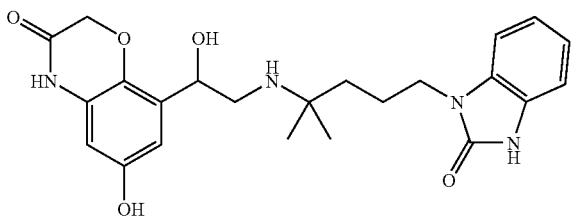

Prepared according to general method 2 from 357 mg (1 mmol) 6-benzyloxy-8-(2-ethoxy-1,2-dihydroxy-ethyl)-4H-benzo[1,4]oxazin-3-one and 233 mg (1 mmol) 1-(4-amino-4-methyl-pentyl)-1,3-dihydro-benzimidazol-2-one. Yield: 192 mg (44%); mass spectroscopy: [M+H]$^+$=441.

Example 7

8-{2-[1,1-dimethyl-3-(2-oxo-benzooxazol-3-yl)-propylamino]-1-hydroxy-ethyl}-6-hydroxy-4H-benzo[1,4]oxazin-3-one

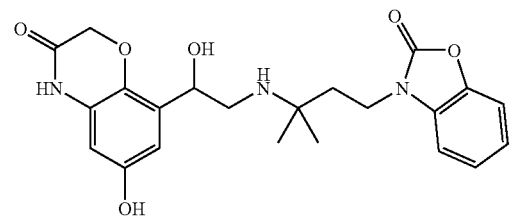

This is prepared according to general method 1 from 357 mg (1 mmol) 6-benzyloxy-8-(2-ethoxy-1,2-dihydroxy-ethyl)-4H-benzo[1,4]oxazin-3-one and 220 mg (1 mmol) 3-(3-amino-3-methyl-butyl)-3H-benzoxazol-2-one.

Yield: 227 mg (42%, trifluoroacetate); mass spectroscopy: [M+H]$^+$=428.

Example 8

7-{2-[1,1-dimethyl-3-(2-oxo-2,3-dihydro-benzimidazol-1-yl)-propylamino]-1-hydroxy-ethyl}-5-hydroxy-3H-benzoxazol-2-one

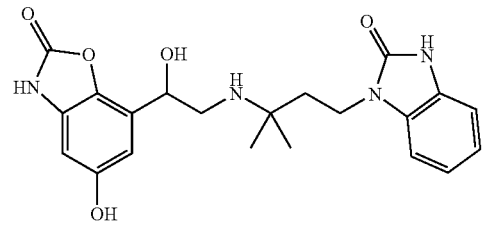

a) 5-benzyloxy-7-{2-[1,1-dimethyl-3-(2-oxo-2,3-dihydro-benzimidazol-1$$ -yl)-propylamino]-1-hydroxy-ethyl}-3H-benzoxazol-2-one 343 mg (1 mmol) 5-benzyloxy-7-(2-ethoxy-2-hydroxy-acetyl)-3H-benzoxazol-2-one and 219 mg (1 mmol) 1-(3-amino-3-methyl-butyl)-1,3-dihydro-benzimidazol-2-one are stirred in 15 mL ethanol for 1.5 hours at 80° C. After cooling to ambient temperature 80 mg (2 mmol) sodium borohydride are added and the mixture is stirred for 2 hours. The reaction mixture is acidified with 3 mL 1 molar hydrochloric acid solution, stirred for 10 minutes and made alkaline with potassium carbonate solution. It is extracted with ethyl acetate, the organic phases are dried with sodium sulphate and the solvent is distilled off. The residue is purified by chromatography over a silica gel column (dichloromethane/methanol gradient). Beige solid. Yield: 340 mg (68%); mass spectroscopy [M+H]$^+$=503.

b) 7-{2-[1,1-dimethyl-3-(2-oxo-2,3-dihydro-benzimidazol-1-yl)-propylamino]-1-hydroxy-ethyl}-5-hydroxy-3H-benzoxazol-2-one 320 mg (0.64 mmol) 5-benzyloxy-7-{2-[1,1-dimethyl-3-(2-oxo-2,3$$ -dihydro-benzimidazol-1-yl)-propylamino]-1- hydroxy-ethyl}-3H-benzoxazol-2-one are dissolved in 12 ml of methanol and hydrogenated with palladium on charcoal as catalyst at ambient temperature. The catalyst is separated off and the filtrate is freed from the solvent. Beige solid. Yield: 150 mg (57%); mass spectroscopy [M-H]+=411.

Example 9

8-{2-[3-(3-benzyl-2-oxo-2,3-dihydro-benzimidazol-1-yl)-1,1-dimethyl-propylamino]-1-hydroxy-ethyl}-6-hydroxy-2,2-dimethyl-4H-benzo[1,4]oxazin-3-one

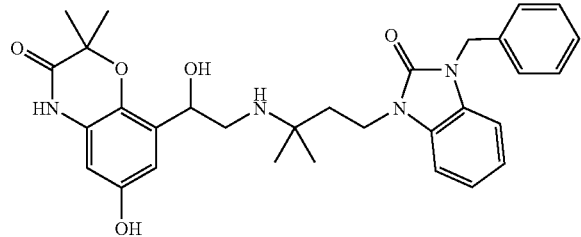

a) 1-(3-amino-3-methyl-butyl)-3-benzyl-1,3-dihydro-benzimidazol-2-one tert-butyl [1,1-Dimethyl-3-(2-oxo-2,3-dihydro-benzimidazol-1-yl)-propyl]-carbamate, benzyl chloride and potassium-tert-butoxide are stirred overnight at ambient temperature in dimethylsulphoxide. The alkylation product tert-butyl [3-(3-benzyl-2-oxo-2,3-dihydro-benzimidazol-1-yl)-1,1-dimethyl-propyl]-carbamate obtained from the reaction is then treated with trifluoroacetic acid/dichloromethane in order to cleave the protective group. Mass spectroscopy [M+H]$^+$=310.

b) 8-{2-[3-(3-benzyl-2-oxo-2,3-dihydro-benzimidazol-1-yl)-1,1-dimethyl-propylamino]-1-hydroxy-ethyl}-6-hydroxy-2,2-dimethyl-4H-benzo[1,4]oxazin-3-one 385 mg (1 mmol) 6-benzyloxy-8-(2-ethoxy-2-hydroxy-acetyl)-2,2-dimethyl-4H-benzo[1,4]oxazin-3-one and 423 mg (1 mmol) 1-(3-amino-3-methyl-butyl)-3-benzyl-1,3-dihydro-benzimidazol-2-one are reacted and worked up according to general method 1.

Yield: 39 mg (6%, trifluoroacetate); mass spectroscopy [M+H]$^+$=545.

Example 10

8-{2-[3-(3-cyclopropylmethyl-2-oxo-2,3-dihydro-benzimidazol-1-yl)-1,1-dimethyl-propylamino]-1-hydroxy-ethyl}-6-hydroxy-4H-benzo[1,4]oxazin-3-one

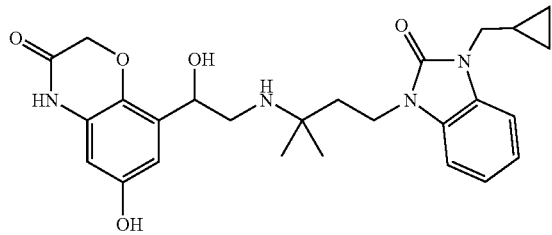

a) 1-(3-amino-3-methyl-butyl)-3-cyclopropylmethyl-1,3-dihydro-benzimidazol-2-one The reaction of tert-butyl [1,1-dimethyl-3-(2-oxo-2,3-dihydro-benzimidazol-1-yl)-propyl]-carbamate with (chloromethyl)-cyclopropane and potassium-tert-butoxide in dimethylsulphoxide at ambient temperature yields tert-butyl [3-(3-cyclopropylmethyl-2-oxo-2,3-dihydro-benzimidazol-1-yl)-1,1-dimethyl-propyl]-carbamate. Then the protective group of the alkylation product is cleaved by treating with trifluoroacetic acid in dichloromethane. Mass spectroscopy [M+H]$^+$=274.

b) 8-{2-[3-(3-cyclopropylmethyl-2-oxo-2,3-dihydro-benzimidazol-1-yl)-1,1$$-dimethyl-propylamino]-1-hydroxy-ethyl}-6-hydroxy-4H-benzo[1,4]oxazin-3-one 165 mg (0.5 mmol) 6-benzyloxy-8-(2-ethoxy-2-hydroxy-acetyl)-4H-benzo[1,4]oxazin-3-one and 194 mg (0.5 mmol) 1-(3-amino-3-methyl-butyl)-3-cyclopropylmethyl-1,3-dihydro-benzimidazol-2-one are dissolved in 8 mL ethanol and stirred for 1.5 hours at 80° C. The mixture is left to cool to ambient temperature, combined with 19 mg (0.5 mmol) sodium borohydride and stirred for a further 2 hours. The reaction mixture is acidified with 1 molar hydrochloric acid, stirred for 10 minutes and made alkaline with potassium carbonate solution. Ethyl acetate is added and the aqueous phase is separated off by filtration through kieselguhr. The organic phase is freed from the solvent and the residue is suspended in acetonitrile/water. The subsequent debenzylation is carried out analogously to general method 1.

Yield: 77 mg (26%, trifluoroacetate); mass spectroscopy [M+H]$^+$=481.

Example 11

5-{2-[1,1-dimethyl-3-(2-oxo-2,3-dihydro-benzimidazol-1-yl)-propylamino]-1-hydroxy-ethyl}-7-hydroxy-1H-quinolin-2-one

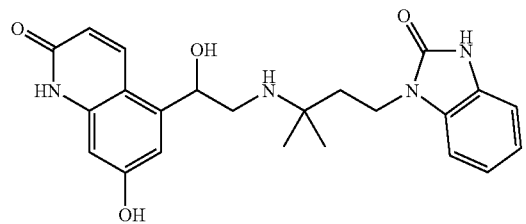

a) 7-benzyloxy-5-{2-[1,1-dimethyl-3-(2-oxo-2,3-dihydro-benzimidazol1$$-yl)-propylamino]-1-hydroxy-ethyl}-1H-quinolin-2-one 121 mg (0.413 mmol) 7-benzyloxy-5-oxiranyl-1H-quinolin-2-one, 125 mg (0.570 mmol) 1-(3-amino-3-methyl-butyl)-1,3-dihydro-benzimidazol-2-one and 0.4 mL isopropanol are combined and irradiated with microwaves for 30 minutes at 135° C. The reaction mixture is combined with ethyl acetate and 0.5 molar tartaric acid, during which time a solid is precipitated. The solid and the aqueous phase are separated off and water, dichloromethane and some methanol are added. The aqueous phase is extracted with dichloromethane and the combined dichloromethane phases are dried and freed from the solvent. The residue is combined with hydrochloric acid in ethyl acetate, the solvent is distilled off and the residue is stirred in ethyl acetate. White solid.

Yield: 87 mg (38%, hydrochloride); mass spectroscopy: [M+H]⁺=513.

b) 5-{2-[1,1-dimethyl-3-(2-oxo-2,3-dihydro-benzimidazol-1-yl)-propylamino]-1-hydroxy-ethyl}-7-hydroxy-1H-quinolin-2-one 71 mg (0.129 mmol) 7-benzyloxy-5-{2-[1,1-dimethyl-3-(2-oxo-2,3$$ -dihydro-benzimidazol-1-yl)-propylamino]-1-hydroxy-ethyl}-1H-quinolin-2-one hydrochloride are dissolved in methanol and hydrogenated at normal pressure with palladium on charcoal as catalyst. The catalyst is separated off by filtration through Celite and the filtrate is freed from solvent. Stirring the residue with ethyl acetate yields the product in the form of a solid. Yield: 31 mg (52%, hydrochloride); mass spectroscopy: [M+H]⁺=423.

Example 12

6-hydroxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one

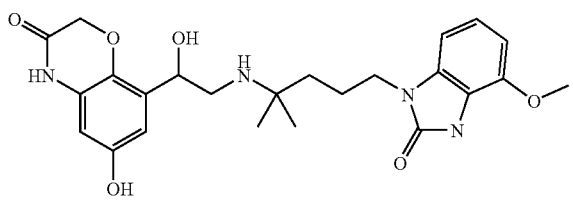

a) 6-benzyloxy-8-{1-hydroxy-2-[4-(4-methoxy-2-oxo-2,3-dihydro-benzimidazol-1-yl)-1,1-dimethyl-butylamino]-ethyl}-4H-benzo[1,4]oxazin-3-one 200 mg (0.667 mmol) of 1-(3-amino-3-methyl-butyl)-4-methoxy-1,3-dihydro-benzimidazol-2-one hydrochloride and 120 µL (0.733 mmol) triethylamine in 5 mL THF are stirred for 30 minutes and then combined with 200 mg (0.666 mmol) 6-benzyloxy-8-(2-ethoxy-2-hydroxy-acetyl)-4H-benzo[1,4]oxazin-3-one. After 2 hours the reaction mixture is cooled to 10° C. cooled and 60 mg (2.76 mmol) lithium borohydride are added. The mixture is stirred for one hour at ambient temperature, then cooled to 10° C. and combined with 15 mL water. The organic phase is extracted with dichloromethane and the combined organic extracts are dried and freed from the solvent. The oil remaining is dissolved in ethyl acetate and adjusted to pH 2 with hydrochloric acid in ethyl acetate. The solvent is distilled off and the residue is stirred with dichloromethane/diethyl ether.

Yield: 130 mg (35%, hydrochloride); mass spectroscopy: [M+H]⁺=561.

b) 6-hydroxy-8-{1-hydroxy-2-[4-(4-methoxy-2-oxo-2,3-dihydro-benzimidazol-1$$ -yl)-1,1-dimethyl-butylamino]-ethyl}-4H-benzo[1,4]oxazin-3-one 130 mg (0.213 mmol) 6-benzyloxy-8-{1-hydroxy-2-[4-(4-methoxy-2-oxo-2,3-dihydro-benzimidazol-1-yl)-1,1-dim-ethyl-butylamino]-ethyl}-4H-benzo[1,4]oxazin-3-one hydrochloride are dissolved in methanol and hydrogenated with palladium on charcoal as catalyst at normal pressure. The catalyst is filtered off through Celite, the filtrate is freed from solvent and the residue is stirred with ethyl acetate. Solid. Yield: 50 mg (45%, hydrochloride); mass spectroscopy: [M+H]⁺=471.

Example 13

6-hydroxy-8-{1-hydroxy-2-[4-(5-methoxy-3-methyl-2-oxo-2,3$$ -dihydro-benzimidazol-1-yl)-1,1-dimethyl-butylamino]-ethyl}-4H-benzo[1,4]oxazin-3-one

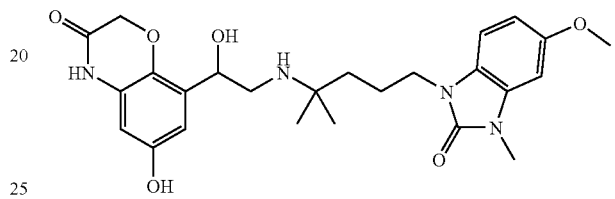

Prepared from 1-(3-amino-3-methyl-butyl)-5-methoxy-3-methyl-1,3-dihydro-benzimidazol-2-one and 6-benzyloxy-8-(2-ethoxy-2-hydroxy-acetyl)-4H-benzo[1,4]oxazin-3-one according to the method described for Example 13. Mass spectroscopy: [M+H]⁺=485.

Example 14

8-{2-[4-(6-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one

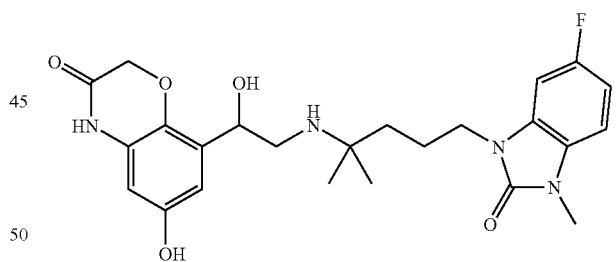

a) 6-benzyloxy-8-{2-[4-(6-fluoro-3-methyl-2-oxo-2,3-dihydro-benzimidazol-1$$ -yl)-1,1-dimethyl-butylamino]-1-hydroxy-ethyl}-4H-benzo[1,4]oxazin-3-one 200 mg (0.754 mmol) 3-(4-amino-4-methyl-pentyl)-5-fluoro-1-methyl-1,3$$ -dihydro-benzimidazol-2-one hydrochloride and 237 mg (0.663 mmol) 6-benzyloxy-8-(2-ethoxy-2-hydroxy-acetyl)-4H-benzo[1,4]oxazin-3-one are reacted analogously to the method described for Example 13a. The final purification is carried out by chromatography on a silica gel column. Yield: 164 mg (44%); mass spectroscopy: [M+H]⁺=563.

b) 8-{2-[4-(6-fluoro-3-methyl-2-oxo-2,3-dihydro-benzimidazol-1-yl)-1,1$$ -dimethyl-butylamino]-1-hydroxy-ethyl}-6-hydroxy-4H-benzo[1,4]oxazin-3-one 164 mg (0.274 mmol) 6-benzyloxy-8-{2-[4-(6-fluoro-3-methyl-2-oxo-2,3$$ -dihydro-benzimidazol-1-yl)-1,1-dimethyl-butylamino]-1-hydroxy-ethyl}-4H-benzo[1,4]oxazin-3-one are debenzylated analogously to the method described for Example 13b. To purify it, the crude product is stirred with ethyl acetate. Mass spectroscopy: [M+H]$^+$=473.

Example 15

8-{2-[4-(7-fluoro-3-methyl-2-oxo-2,3-dihydro-benzimidazol-1-yl)-1,1-dimethyl-butylamino]-1-hydroxy-ethyl}-6-hydroxy-4H-benzo[1,4]oxazin-3-one

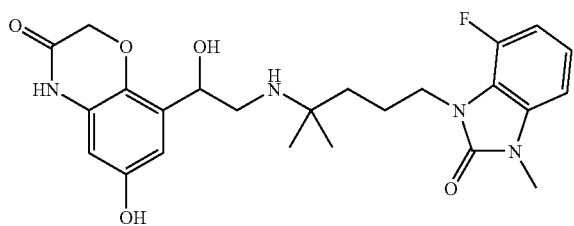

a) 6-benzyloxy-8-{2-[4-(7-fluoro-3-methyl-2-oxo-2,3-dihydro-benzimidazol-1$$ -yl)-1,1-dimethyl-butylamino]-1-hydroxy-ethyl}-4H-benzo[1,4]oxazin-3-one 200 mg (0.663 mmol) 3-(4-amino-4-methyl-pentyl)-4-fluoro-1-methyl-1,3$$ -dihydro-benzimidazol-2-one hydrochloride and 237 mg (0.663 mmol) 6-benzyloxy-8-(2-ethoxy-2-hydroxy-acetyl)-4H-benzo[1,4]oxazin-3-one are reacted analogously to the method described for preparing Example 13a. The final purification of the product is carried out by chromatography on a silica gel column.

Yield: 68 mg (17%); mass spectroscopy: [M+H]$^+$=563.

b) 8-{2-[4-(7-fluoro-3-methyl-2-oxo-2,3-dihydro-benzimidazol-1-yl)-1,1$$ -dimethyl-butylamino]-1-hydroxy-ethyl}-6-hydroxy-4H-benzo[1,4]oxazin-3-one 68 mg (0.121 mmol) 6-benzyloxy-8-{2-[4-(7-fluoro-3-methyl-2-oxo-2,3$$ -dihydro-benzimidazol-1-yl)-1,1-dimethyl-butylamino]-1-hydroxy-ethyl}-4H-benzo[1,4]oxazin-3-one are debenzylated according to the method described for Example 13b. For purification the crude product is stirred in ethyl acetate. Yield: 60 mg; mass spectroscopy: [M+H]$^+$=474.

Suitable preparations for administering the compounds of formula 1 include for example tablets, capsules, suppositories, solutions, powders, etc. The content of the pharmaceutically active compound(s) should be in the range from 0.05 to 90 wt.-%, preferably 0.1 to 50 wt.-% of the composition as a whole. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations of active substances according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions are prepared in the usual way, e.g. with the addition of isotonic agents, preservatives such as p-hydroxybenzoates or stabilisers such as alkali metal salts of ethylenediaminetetraacetic acid, optionally using emulsifiers and/or dispersants, while if water is used as diluent, for example, organic solvents may optionally be used as solubilisers or dissolving aids, and the solutions may be transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral use the tablets may obviously contain, in addition to the carriers specified, additives such as sodium citrate, calcium carbonate and dicalcium phosphate together with various additional substances such as starch, preferably potato starch, gelatine and the like. Lubricants such as magnesium stearate, sodium laurylsulphate and talc may also be used to produce the tablets. In the case of aqueous suspensions the active substances may be combined with various flavour enhancers or colourings in addition to the abovementioned excipients.

In the preferred use of the compounds of formula 1 for the treatment of respiratory complaints according to the invention it is particularly preferred to use preparations or pharmaceutical formulations which are suitable for inhalation. Inhalable preparations include inhalable powders, propellant-containing metered-dose aerosols or propellant-free inhalable solutions. Within the scope of the present invention, the term propellant-free inhalable solutions also includes concentrates or sterile ready-to-use inhalable solutions. The formulations which may be used within the scope of the present invention are described in more detail in the next part of the specification.

The inhalable powders which may be used according to the invention may contain 1 either on its own or in admixture with suitable physiologically acceptable excipients.

If the active substances 1 are present in admixture with physiologically acceptable excipients, the following physiologically acceptable excipients may be used to prepare these inhalable powders according to the invention: monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these excipients. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred.

Within the scope of the inhalable powders according to the invention the excipients have a maximum average particle size of up to 250 μm, preferably between 10 and 150 μm, most preferably between 15 and 80 μm. In some cases it may seem appropriate to add finer excipient fractions with an average particle size of 1 to 9 μm to the excipients mentioned above. These finer excipients are also selected from the group of possible excipients listed hereinbefore. Finally, in order to prepare the inhalable powders according to the invention, micronised active substance 1, preferably with an average particle size of 0.5 to 10 μm, more preferably from 1 to 5 μm, is added to the excipient mixture. Processes for producing the inhalable powders according to the invention by grinding and micronising and lastly mixing the ingredients together are known from the prior art.

The inhalable powders according to the invention may be administered using inhalers known from the prior art.

The inhalation aerosols containing propellant gas according to the invention may contain the compounds 1 dissolved in the propellant gas or in dispersed form. The propellant gases which may be used to prepare the inhalation aerosols are known from the prior art. Suitable propellant gases are selected from among hydrocarbons such as n-propane, n-butane or isobutane and halohydrocarbons such as fluorinated derivatives of methane, ethane, propane, butane, cyclopropane or cyclobutane. The above-mentioned propellant gases may be used on their own or mixed together. Particularly preferred propellant gases are halogenated alkane derivatives selected from TG134a and TG227 and mixtures thereof.

The propellant-driven inhalation aerosols may also contain other ingredients such as co-solvents, stabilisers, surfactants, antioxidants, lubricants and pH adjusters. All these ingredients are known in the art.

The propellant-driven inhalation aerosols mentioned above may be administered using inhalers known in the art (MDIs=metered dose inhalers).

Moreover, the active substances 1 according to the invention may be administered in the form of propellant-free inhalable solutions and suspensions. The solvent used may be an aqueous or alcoholic, preferably an ethanolic solution. The solvent may be water on its own or a mixture of water and ethanol. The relative proportion of ethanol compared with water is not limited but the maximum is preferably up to 70 percent by volume, more particularly up to 60 percent by volume and most preferably up to 30 percent by volume. The remainder of the volume is made up of water. The solutions or suspensions containing 1 are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

If desired, the addition of editic acid (EDTA) or one of the known salts thereof, sodium edetate, as stabiliser or complexing agent may be omitted in these formulations. Other embodiments may contain this compound or these compounds. In a preferred embodiment the content based on sodium edetate is less than 100 mg/100 ml, preferably less than 50 mg/100 ml, more preferably less than 20 mg/100 ml. Generally, inhalable solutions in which the content of sodium edetate is from 0 to 10 mg/100 ml are preferred.

Co-solvents and/or other excipients may be added to the propellant-free inhalable solutions. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the physiologically suitable solvent in order to improve the qualitative properties of the active substance formulation. Preferably, these substances have no pharmacological effect or, in connection with the desired therapy, no appreciable or at least no undesirable pharmacological effect. The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents.

The preferred excipients include antioxidants such as ascorbic acid, for example, provided that it has not already been used to adjust the pH, vitamin A, vitamin E, tocopherols and similar vitamins and provitamins occurring in the human body.

Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art. The preservatives mentioned above are preferably present in concentrations of up to 50 mg/100 ml, more preferably between 5 and 20 mg/100 ml.

Preferred formulations contain, in addition to the solvent water and the active substance 1, only benzalkonium chloride and sodium edetate.

In another preferred embodiment, no sodium edetate is present.

The dosage of the compounds according to the invention is naturally highly dependent on the method of administration and the complaint which is being treated. When administered by inhalation the compounds of formula 1 are characterised by a high potency even at doses in the μg range. The compounds of formula 1 may also be used effectively above the μg range. The dosage may then be in the milligram range, for example.

In another aspect the present invention relates to the above-mentioned pharmaceutical formulations as such, which are characterised in that they contain a compound of formula 1, particularly preferably the above-mentioned pharmaceutical formulations administered by inhalation.

The following examples of formulations illustrate the present invention without restricting its scope:

| A) Ampoule solution | |
|---|---|
| active substance of formula 1 | 25 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| B) Metered-dose aerosol (suspension) | |
|---|---|
| active substance of formula 1 | 0.3 wt. % |
| sorbitolan trioleate | 0.6 wt. % |
| HFA134A:HFA227 2:1 | 99.1 wt. % |

The suspension is transferred into a conventional aerosol container with a metering valve. Preferably, 50 μl of suspension are delivered per spray. The active substance may also be metered in higher doses if desired.

| C) Metered-dose aerosol (solution) | |
|---|---|
| active substance of formula 1 | 0.3 wt. %.% |
| abs. ethanol | 20 wt. % |
| aqueous HCl 0.01 mol/l | 2.0 wt. % |
| HFA134A | 77.7 wt. % |

The solution is produced in the usual way by mixing the individual ingredients together.

| D) Inhalable powder | |
|---|---|
| active substance of formula 1 | 80 μg |
| lactose monohydrate | ad 10 mg |

The powder for inhalation is produced in the usual way by mixing the individual ingredients together.

The invention claimed is:

1. A Compound of formula 1

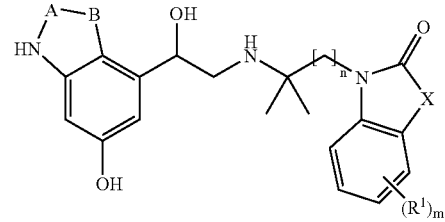

wherein
n denotes 1 or 4;
m denotes 1, 2 or 3;
X denotes $CH_2$, CO, $NR^2$, S or O;
A denotes a double-bonded group selected from the group consisting of CO, SO and $SO_2$;
B denotes a double-bonded group selected from the group consisting of O, S, $CH_2$, $CR^3R^4$—O, $CR^3R^4$—S, $NR^5$, $CR^3R^4$—$NR^5$, CH=CH and $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C^{1-6}$-haloalkyl, halogen, OH, CN, $NO_2$, O—$C_{1-6}$-alkyl, COOH or COO—$C_{1-4}$-alkyl;
$R^2$ denotes H, $C^{1-6}$-alkyl, $C_{1-4}$-alkylene-$C_6$-$C_{10}$-aryl or $C_{1-4}$-alkylene-$C_{3-6}$-cycloalkyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

2. A Compound of formula 1

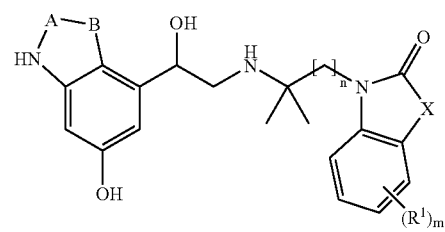

wherein
n denotes 1, 3 or 4;
m denotes 1, 2 or 3;
X denotes $CH_2$, CO, $NR^2$, S or O;
A denotes a double-bonded group selected from the group consisting of CO, SO and $SO^2$;
B denotes a double-bonded group selected from the group consisting of O, S, $CH_2$, $CR^3R^4$—O, $CR^3R^4$—S, $NR^5$, $CR^3R^4$—$NR^5$, CH=CH and $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH or COO—$C_{1-4}$-alkyl;
$R^2$ denotes $C_{1-6}$-alkyl, $C_{1-4}$-alkylene-$C_6$—$C_{10}$-aryl or $C_{1-4}$-alkylene-$C_{3-6}$-cycloalkyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

3. A Compound of formula 1

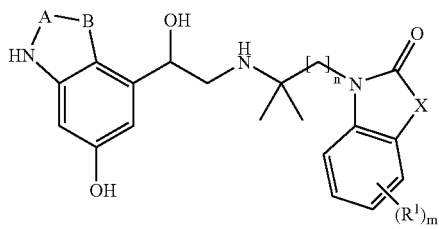

wherein
n denotes 1,2, or 4;
m denotes 1,2 or 3;
X denotes $CH_2$, CO, $NR_2$, S or O;
A denotes a double-bonded group selected from the group consisting of CO, SO and $SO_2$;
B denotes a double-bonded group selected from the group consisting of S, $CH_2$, $CR^3R^4$—O, $CR^3R^4$—S, $NR^5$, $CR^3R^4$—$NR^5$, CH=CH and $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH or COO—$C_{1-4}$-alkyl;
$R^2$ denotes H, $C_{1-4}$-alkylene-$C_6$—$C_{10}$-aryl or $C_{1-4}$-alkylene-$C_{3-6}$-cycloalkyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

4. The compound of formula 1, according to claim 1, wherein
n denotes 1 or 4;
m denotes 1,2 or 3;
X denotes $CH_2$, CO, $NR_2$, S or O;
A denotes CO;
B denotes a double-bonded group selected from the group consisting of O, S, $CH_2$, $CR^3R^4$—O, $CR^3R^4$—S, $NR^5$, $CR^3R^4$—$NR^5$, CH=CH and $CH_2$—$CH_2$;
$R^1$ denotes H, $C_{1-6}$-alkyl, $C_{1-6}$-haloalkyl, $C_{3-6}$-cycloalkyl, halogen, OH,CN, $NO_2$, O—$C_{1-6}$-alkyl, COOH or COO—$C_{1-4}$-alkyl;
$R^2$ denotes H, $C_{1-4}$-alkyl, $C_{1-2}$-alkylene-$C_{3-6}$-cycloalkyl, phenylethyl or benzyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

5. The compound of formula 1, according to claim 1, wherein
X denotes $NR^2$ or O; or an acid addition salt thereof with a pharmacologically acceptable acid.

6. The compound of formula 1, according to claim 1, wherein
n denotes 3;
m denotes 1;
X denotes $CH_2$, CO, $NR^2$, S or O;
A denotes CO;
B denotes a double-bonded group selected from the group consisting of $CH_2$—O, CH=CH and $CH_2$—$CH_2$;
$R^1$ denotes H, methyl or $CF_3$;
$R^2$ denotes methyl;
or an acid addition salt thereof with a pharmacologically acceptable acid.

7. The compound of formula 1, according to claim 2, wherein
n denotes 3;
m denotes 1 or 2;
X denotes $CH_2$, CO, $NR^2$, S or O;
A denotes CO;
B denotes a double-bonded group selected from the group consisting of $CH_2$—O, CH=CH and $CH_2$—$CH_2$;
$R^1$ denotes H, methyl, ethyl, propyl, $CF_3$, $CH_2F$ or $CH_2CF_3$;
$R^2$ denotes methyl, ethyl or propyl;
or an acid addition salt thereof with a pharmacologically acceptable acid.

8. The compound of formula 1, according to claim 2, wherein
n denotes 1, 3 or 4;
m denotes 1, 2 or 3;
X denotes $CH_2$, CO, $NR^2$, S or O;
A denotes CO;
B denotes a double-bonded group selected from the group consisting of O, S, $CH_2$, $CR^3R^4$—O, $CR^3R^4$—S, $NR^5$, $CR^3R^4$—$NR^5$, CH=CH and $CH_2$—$CH_2$;
$R^1$ denotes H, $C_{1-6}$-alkyl, $C_{1-6}$-haloalkyl, $C_{3-6}$-cycloalkyl, halogen, OH, CN, $NO_2$, O—$C_{1-6}$-alkyl, COOH or COO—$C_{1-4}$-alkyl;
$R^2$ denotes $C_{1-4}$-alkyl, $C_2$-alkylene-$C_{3-6}$-cycloalkyl, phenylethyl or benzyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

9. The compound of formula 1, according to claim 2, wherein
n denotes 3;
m denotes 1, 2 or 3;
X denotes $CH_2$, CO, $NR^2$, S or O;
A denotes CO;
B denotes a double-bonded group selected from the group consisting of O, S, $CH_2$, $CR^3R^4$—O, $CR^3R^4$—S, $NR^5$, $CR^3R^4$—$NR^5$, CH=CH and $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes methyl, ethyl or propyl;
$R^3$ denotes H, methyl, ethyl or propyl;
$R^4$ denotes H, methyl, ethyl or propyl;
$R^5$ denotes H, methyl, ethyl or propyl;
or an acid addition salt thereof with a pharmacologically acceptable acid.

10. The compound of formula 1, according to claim 2, wherein
n denotes 3;
m denotes 1, 2 or 3;
X denotes $CH_2$, CO, $NR^2$, S or O;
A denotes CO;
B denotes a double-bonded group selected from the group consisting of $CH_2$—O, CH=CH and $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes methyl, ethyl or propyl;
or an acid addition salt thereof with a pharmacologically acceptable acid.

11. The compound of formula 1, according to claim 2, wherein
X denotes $NR^2$ or O;
or an acid addition salt thereof with a pharmacologically acceptable acid.

12. The compound of formula 1, according to claim 11, wherein
n denotes 3;
m denotes 1;
A denotes CO;
B denotes a double-bonded group selected from the group consisting of $CH_2$—O and CH=CH;
$R^1$ denotes H, methyl or $CF_3$;
$R^2$ denotes methyl;
or an acid addition salt thereof with a pharmacologically acceptable acid.

13. The compound of formula 1, according to claim 3, wherein
n denotes 1, 2 or 4;
m denotes 1, 2 or 3;
X denotes $CH_2$, CO, $NR^2$, S or O;
A denotes CO;
B denotes a double-bonded group selected from the group consisting of S, $CH_2$, $CR^3R^4$—O, $CR^3R^4$—S, $NR^5$, $CR^3R^4$—$NR^5$, CH=CH and $CH_2$—$CH_2$;
$R^1$ denotes H, $C^{1-6}$-alkyl, $C_{1-6}$-haloalkyl, $C_{3-6}$-cycloalkyl, halogen, OH, CN, $NO_2$, O—$C_{1-6}$-alkyl, COOH or COO—$C_{1-4}$-alkyl;
$R^2$ denotes H, $C_{1-2}$-alkylene-$C_{3-6}$-cycloalkyl, phenylethyl or benzyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

14. The compound of formula 1, according to claim 3, wherein
n denotes 2;
m denotes 1, 2 or 3;
X denotes $CH_2$, CO, $NR^2$, S or O;
A denotes CO;
B denotes a double-bonded group selected from the group consisting of S, $CH_2$, $CR_3R_4$—O, $CR^3R^4$—S, $NR^5$, $CR^3R^4$—$NR^5$, CH=CH and $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H;
$R^3$ denotes H, methyl, ethyl or propyl;
$R^4$ denotes H, methyl, ethyl or propyl;
$R^5$ denotes H, methyl, ethyl or propyl;
or an acid addition salt thereof with a pharmacologically acceptable acid.

15. The compound of formula 1, according to claim 3, wherein
n denotes 2;
m denotes 1, 2 or 3;
X denotes $CH_2$, CO, $NR^2$, S or O;
A denotes CO;
B denotes a double-bonded group selected from the group consisting of $CH_2$—O, CH=CH and $CH_2$—$CH_2$;
$R^1$ denotes H, methyl, ethyl, propyl, $CF_3$, $CH_2F$, $CH_2CF_3$, fluorine, chlorine, bromine, OH, methoxy, ethoxy, COOH or COOMe;
$R^2$ denotes H;
or an acid addition salt thereof with a pharmacologically acceptable acid.

16. The compound of formula 1, according to claim 3, wherein
n denotes 2;
m denotes 1 or 2;
X denotes $CH_2$, CO, $NR^2$, S or O;
A denotes CO;
B denotes a double-bonded group selected from the group consisting of $CH_2$—O, CH=CH and $CH_2$—$CH_2$;
$R^1$ denotes H, methyl, ethyl, propyl, $CF_3$, $CH_2F$ or $CH_2CF_3$;
$R^2$ denotes H;
or an acid addition salt thereof with a pharmacologically acceptable acid.

17. The compound of formula 1, according to claim 3, wherein
n denotes 2;
m denotes 1;
X denotes $CH_2$, CO, $NR^2$, S or O;
A denotes CO;
B denotes a double-bonded group selected from the group consisting of $CH_2$—O, CH=CH and $CH_2$—$CH_2$;
$R^1$ denotes H, methyl or $CF_3$;
$R^2$ denotes H;
or an acid addition salt thereof with a pharmacologically acceptable acid.

18. The compound of formula 1, according to claim 3, wherein
X denotes $NR^2$ or O;
or an acid addition salt thereof with a pharmacologically acceptable acid.

19. The compound of formula 1, according to claim 18, wherein
n denotes 2;
m denotes 1;
A denotes CO;
B denotes a double-bonded group selected from the group consisting of $CH_2$—O and CH=CH;
$R^1$ denotes H, methyl or $CF_3$;
$R^2$ denotes H;
or an acid addition salt thereof with a pharmacologically acceptable acid.

20. The compound of formula 1, according to claim 19, wherein
n denotes 2;
m denotes 1;
X denotes NH;
A denotes CO;
B denotes a double-bonded group $CH_2$—O;
$R^1$ denotes H, methyl or $CF_3$;
or an acid addition salt thereof with a pharmacologically acceptable acid.

21. The compound of formula 1, according to any of claims 1, 2 or 3, wherein
A denotes CO;
or an acid addition salt thereof with a pharmacologically acceptable acid.

22. The compound of formula 1 according to any one of claims 1, 2 or 3, characterised in that the compound is in the form of an acid addition salt with a pharmacologically acceptable acid which is selected from the group consisting of hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate.

23. The compound of formula 1 according to any one of claims 1, 2 or 3, characterised in that the compound is in the form of the R-enantiomer of formula R-1

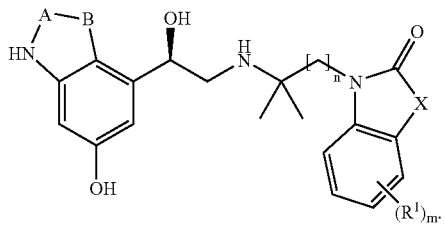

24. A pharmaceutical composition, which comprises a compound of formula 1

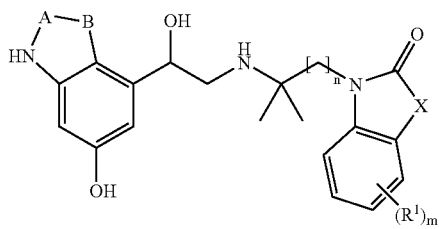

wherein
n denotes 1, 2, 3 or 4;
m denotes 1, 2 or 3;
X denotes $CH_2$, CO. $NR^2$, S or O;
A denotes a double-bonded group selected from the group consisting of CO, SO and $SO_2$;
B denotes a double-bonded group selected from the group consisting of O, S, $CH_2$, $CR^3R^4$—O, $CR^3R^4$—S, $NR^5$, CH=CH and $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH or COO—$C_{1-4}$-alkyl;
$R^2$ denotes H, $C_{1-6}$-alkyl, $C_{1-4}$-alkylene-$C_6$—$C_{1-10}$-aryl or $C_{1-4}$-alkylene-$C_{3-6}$-cycloalkyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid; and a pharmaceutically acceptable carrier or excipient;

wherein said amount of said compound of formula 1 is therapeutically effective for treating a respiratory complaint selected from the group consisting of:
(A): an obstructive pulmonary disease;
(B): a restrictive pulmonary disease;
(C): an interstitial pulmonary disease;
(D): cystic fibrosis;
(E): bronchitis;
(F): bronchiectasis;
(G): ARDS (Adult Respiratory Distress Syndrome); and
(H): pulmonary oedema.

25. A method of treating a respiratory complaint selected from the group consisting of:
(A): an obstructive pulmonary disease;
(B): a restrictive pulmonary disease;
(C): an interstitial pulmonary disease;
(D): cystic fibrosis;
(E): bronchitis;
(F): bronchiectasis;
(G): ARDS (Adult Respiratory Distress Syndrome); and
(H): pulmonary oedema;
which comprises administering a therapeutically effective amount of a compound of formula 1

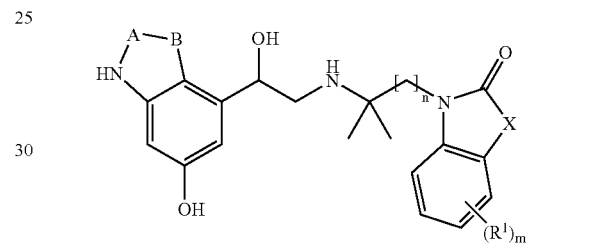

wherein
n denotes 1, 2, 3 or 4;
m denotes 1, 2 or 3;
X denotes $CH_2$, CO, $NR^2$, S or O;
A denotes a double-bonded group selected from the group consisting of CO, SO and $SO_2$;
B denotes a double-bonded group selected from the group consisting of O, S, $CH_2$, $CR^3R^4$—O, $CR^3R^4$—S, $NR^5$, CH=CH and $CH_2$—$CH_2$;
$R^1$ denotes H, $C_{1-6}$-alkyl, $C_{2-6}$-alkenyl, $C_{2-6}$-alkynyl, $C_{3-6}$-cycloalkyl, $C_{1-6}$-haloalkyl, O—$C_{1-6}$-haloalkyl, halogen, OH, CN, $NO_2$, O—$C_{1-6}$-alkyl, COOH or COO—$C_{1-4}$-alkyl;
$R^2$ denotes H, $C_{1-6}$-alkyl, $C_{1-4}$-alkylene-$C_6$-$C_{10}$-aryl or $C_{1-4}$-alkylene-$C_{3-6}$-cycloalkyl;
$R^3$ denotes H or $C_{1-6}$-alkyl;
$R^4$ denotes H or $C_{1-6}$-alkyl;
$R^5$ denotes H or $C_{1-6}$-alkyl;
or an acid addition salt thereof with a pharmacologically acceptable acid.

* * * * *